US012398422B2

(12) United States Patent
Modiano et al.

(10) Patent No.: US 12,398,422 B2
(45) Date of Patent: Aug. 26, 2025

(54) FLUIDIC DEVICES INCLUDING FLUIDIC CHANNELS, AND METHODS OF MAKING THE SAME

(71) Applicant: ILLUMINA, INC., San Diego, CA (US)

(72) Inventors: Steven Modiano, San Diego, CA (US); Silke Musa, La Jolla, CA (US); Lewis Kraft, Acworth, GA (US); Randall Smith, San Marcos, CA (US); Sara Bakhshi, San Diego, CA (US); Brian Mather, San Diego, CA (US); Wayne George, Ilford (GB); Maxwell Zimmerley, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 776 days.

(21) Appl. No.: 17/743,969

(22) Filed: May 13, 2022

(65) Prior Publication Data

US 2022/0380844 A1 Dec. 1, 2022

Related U.S. Application Data

(60) Provisional application No. 63/194,330, filed on May 28, 2021.

(51) Int. Cl.
*C12Q 1/6874* (2018.01)
*B01L 3/00* (2006.01)

(52) U.S. Cl.
CPC ...... *C12Q 1/6874* (2013.01); *B01L 3/502761* (2013.01); *B01L 2200/0647* (2013.01); *B01L 2200/12* (2013.01)

(58) Field of Classification Search
CPC ............ C12Q 1/6874; B01L 3/502761; B01L 2200/0647; B01L 2200/12;
(Continued)

(56) References Cited

U.S. PATENT DOCUMENTS 8,546,598 B2 10/2013 Bernardin et al.
10,208,142 B2 2/2019 Brown et al.
(Continued)

FOREIGN PATENT DOCUMENTS

WO WO-2021087402 A1 * 5/2021 ........ B01L 3/502707

OTHER PUBLICATIONS

You et al "A doubly cross-linked nano-adhesive for the reliable sealing of flexible microfluidic devices", Lab on a Chip, vol. 13, No. 7, Jan. 1, 2013, p. 1266 (Year: 2013).*
(Continued)

*Primary Examiner* — Dennis White
(74) *Attorney, Agent, or Firm* — Sheppard, Mullin, Richter & Hampton LLP; Jaime D. Choi

(57) ABSTRACT

In one example, a method of preparing a fluidic channel includes covalently coupling a first region of a substrate to a first region of a cover using first moieties covalently coupled to the first region of the substrate and second moieties covalently coupled to the first region of the cover. The covalent coupling between the first region of the substrate and the first region of the cover suspends a second region of the cover over a second region of the substrate to form a fluidic channel.

21 Claims, 13 Drawing Sheets

(58) Field of Classification Search
CPC ......... B01L 3/502707; C08J 5/12; C09J 5/02; C09J 5/06; C09J 5/00
See application file for complete search history.

(56) References Cited

U.S. PATENT DOCUMENTS 10,388,587 B1    8/2019   Smith et al.
2020/0009556 A1  1/2020   Zimmerley et al.

OTHER PUBLICATIONS

Rambarran et al "Bonding and in-channel microfluidic functionalization using the huisgen cyclization", Journal of Polymer Science Part A: Polymer Chemistry, vol. 56, No. 6, Mar. 15, 2018 (Mar. 15, 2018), pp. 589-597 (Year: 2018).*
Dommerholt et al., "Strain-Promoted 1,3-Dipolar Cycloaddition of Cycloalkynes and Organic Azides," Top Curr Chem (Z); 374:16: 1-20 (2016).
Gan et al., "Photoactivation of alkyl C-H and silanization: A simple and general route to prepare high-density primary amines on inert polymer surfaces for protein immobilization," Biomacromolecules; 10(5): 1238-1243 (2009).
International Search Report and Written Opinion for PCT/US2022/029187 dated Aug. 29, 2022; 16 pages.
Rambarran et al., "Bonding and in-channel microfluidic functionalization using the huisgen cyclization," Journal of Polymer Science Part A: Polymer Chemistry; 56(6): 589-597 (2018).
You et al., "A doubly cross-linked nano-adhesive for the reliable sealing of flexible microfluidic devices," Lab on a Chip; 13(7): 1266-1272 (2013).

* cited by examiner

FLUIDIC DEVICES INCLUDING FLUIDIC CHANNELS, AND METHODS OF MAKING THE SAME

CROSS-REFERENCE TO RELATED APPLICATION

This application claims the benefit of U.S. Provisional Patent Application No. 63/194,330, filed May 28, 2021 and entitled "Fluidic Devices Including Fluidic Channels, and Methods of Making the Same," the entire contents of which are incorporated by reference herein.

FIELD

This application generally relates to devices including fluidic channels.

BACKGROUND

Fluidic channels are used in many technological applications. For example, certain molecular analyses, such as certain polynucleotide sequencing methods, utilize polynucleotides that are coupled within a fluidic channel (sometimes referred to as a flow cell). For example, oligonucleotide primers (e.g., single stranded DNA or ssDNA) may be grafted to the fluidic channel and used to amplify target polynucleotides for sequencing. Fluidic channels may be formed by coupling covers, which may be formed of glass or plastic, substrates using adhesives such as pressure sensitive adhesives or epoxies. However, such adhesives may chemically react with fluid(s) within the fluidic channel, may fluoresce in such a way that interferes with detection of a desired fluorescent signal, and/or may be thermally unstable, thus potentially resulting in fluidic leaks or other damage. Accordingly, what is needed is an improved way to make fluidic channels, e.g., that may include dissimilar materials.

SUMMARY

Examples provided herein are related to devices including fluidic channels and methods of making the same.

Some examples herein provide a method of preparing a fluidic channel. The method may include covalently coupling a first region of a substrate to a first region of a cover using first moieties covalently coupled to the first region of the substrate and second moieties covalently coupled to the first region of the cover. The covalent coupling between the first region of the substrate and the first region of the cover may suspend a second region of the cover over a second region of the substrate to form a fluidic channel.

In some examples, the method further includes comprising coupling oligonucleotides to the second region of the substrate. In some examples, the oligonucleotides are coupled to the second region of the substrate before the first region of the substrate is coupled to the first region of the cover. In some examples, the method further includes protecting the oligonucleotides before the first region of the substrate is covalently coupled to the first region of the cover. In some examples, protecting the oligonucleotides comprises depositing a mask over the oligonucleotides. In some examples, the method further includes removing the mask after the first region of the substrate is covalently coupled to the first region of the cover. In some examples, the oligonucleotides are covalently coupled to the second region of the substrate using second moieties covalently coupled to the second region of the substrate. In some examples, the oligonucleotides comprise capture primers. In some examples, the oligonucleotides are coupled to the second region of the substrate after the first region of the substrate is coupled to the first region of the cover.

In some examples, covalently coupling the first region of the substrate to the first region of the cover comprises selectively applying heat to the first region of the substrate or the first region of the cover. In some examples, the heat is applied using light. In some examples, the light includes an infrared or near-infrared wavelength.

In some examples, covalently coupling the first region of the substrate to the first region of the cover comprises applying pressure to the first region of the substrate and the first region of the cover.

In some examples, covalently coupling the first region of the substrate to the first region of the cover comprises reacting the first moieties with the second moieties. In some examples, the reaction between the first moieties and the second moieties comprises an azide-alkyne [3+2] cyclo-addition.

In some examples, the method further includes disposing an intervening layer between the first region of the substrate and the first region of the cover. Covalently coupling the first region of the substrate to the first region of the cover may include covalently coupling the first region of the substrate to the intervening layer; and covalently coupling the first region of the cover to the intervening layer. In some examples, the intervening layer comprises the first moieties or the second moieties. In some examples, covalently coupling the first region of the substrate to the intervening layer comprises a comprises a first azide-alkyne [3+2] cyclo-addition. In some examples, covalently coupling the first region of the cover to the intervening layer comprises a second azide-alkyne [3+2] cyclo-addition.

In some examples, the first moieties are covalently coupled to the first region of the substrate via silane groups, carboxylate groups, or amidate groups. In some examples, the second moieties are covalently coupled to the second region of the substrate via silane groups, carboxylate groups, or amidate groups.

In some examples, the cover comprises a different material than the substrate. In some examples, the cover comprises at least one material selected from the group consisting of: cyclic olefin polymer (COP), cyclic olefin copolymer (COC), glass, silicon, polypropylene (PP), photoresist, polyethylene terephthalate (PET), poly(N-(5-azidoacetamidylpentyl) acrylamide-co-acrylamide) (PAZAM), and polyethylene (PE). In some examples, the substrate comprises at least one material selected from the group consisting of: cyclic olefin polymer (COP), cyclic olefin copolymer (COC), glass, silicon, polypropylene (PP), photoresist, polyethylene terephthalate (PET), poly(N-(5-azidoacetamidylpentyl) acrylamide-co-acrylamide) (PAZAM), and polyethylene (PE). In some examples, the second region of the cover is separated from the second region of the substrate by between about 1 µm and about 1 cm.

Some examples herein provide a fluidic device that includes a substrate comprising a first region and a second region; and a cover comprising a first region and a second region. The first region of the substrate may be covalently coupled to the first region of the cover using first moieties covalently coupled to the first region of the substrate and second moieties covalently coupled to the first region of the cover. The covalent coupling between the first region of the substrate and the first region of the cover suspends the second region of the cover over the second region of the substrate to form a fluidic channel.

In some examples, the device further includes oligonucleotides coupled to the second region of the substrate. In some examples, the oligonucleotides are covalently coupled to the second region of the substrate using second moieties covalently coupled to the second region of the substrate. In some examples, the oligonucleotides comprise capture primers.

In some examples, the first region of the substrate is covalently coupled to the first region of the cover via the product of an azide-alkyne [3+2] cyclo-addition reaction between the first moieties and the second moieties.

In some examples, the device further includes an intervening layer between the first region of the substrate and the first region of the cover, wherein the first region of the substrate is covalently coupled to the intervening layer, and wherein the first region of the cover is covalently coupled to the intervening layer. In some examples, the intervening layer comprises the first moieties or the second moieties. In some examples, the first region of the substrate is covalently coupled to the intervening layer via the product of an azide-alkyne [3+2] cyclo-addition reaction. In some examples, the first region of the cover is covalently coupled to the intervening layer via the product of an azide-alkyne [3+2] cyclo-addition reaction.

In some examples, the first moieties are covalently coupled to the first region of the substrate via silane groups, carboxylate groups, or amidate groups. In some examples, the second moieties are covalently coupled to the second region of the cover via silane groups, carboxylate groups, or amidate groups.

In some examples, the cover comprises a different material than the substrate. In some examples, the substrate comprises at least one material selected from the group consisting of: cyclic olefin polymer (COP), cyclic olefin copolymer (COC), glass, silicon, polypropylene (PP), photoresist, polyethylene terephthalate (PET), poly(N-(5-azidoacetamidylpentyl) acrylamide-co-acrylamide) (PAZAM), and polyethylene (PE). In some examples, the cover comprises at least one material selected from the group consisting of: cyclic olefin polymer (COP), cyclic olefin copolymer (COC), glass, silicon, polypropylene (PP), photoresist, polyethylene terephthalate (PET), poly(N-(5-azidoacetamidylpentyl) acrylamide-co-acrylamide) (PAZAM), and polyethylene (PE). In some examples, the second region of the cover is separated from the second region of the substrate by between about 1 μm and about 1 cm.

Some examples herein provide a method of making the above-described device, in which the first region of the substrate is covalently coupled to the first region of the cover using selectively application of heat to the first region of the substrate or the first region of the cover.

In some examples, the heat is applied using light. The light may include an infrared or near-infrared wavelength.

It is to be understood that any respective features/examples of each of the aspects of the disclosure as described herein may be implemented together in any appropriate combination, and that any features/examples from any one or more of these aspects may be implemented together with any of the features of the other aspect(s) as described herein in any appropriate combination to achieve the benefits as described herein.

DETAILED DESCRIPTION

Figure 1A:
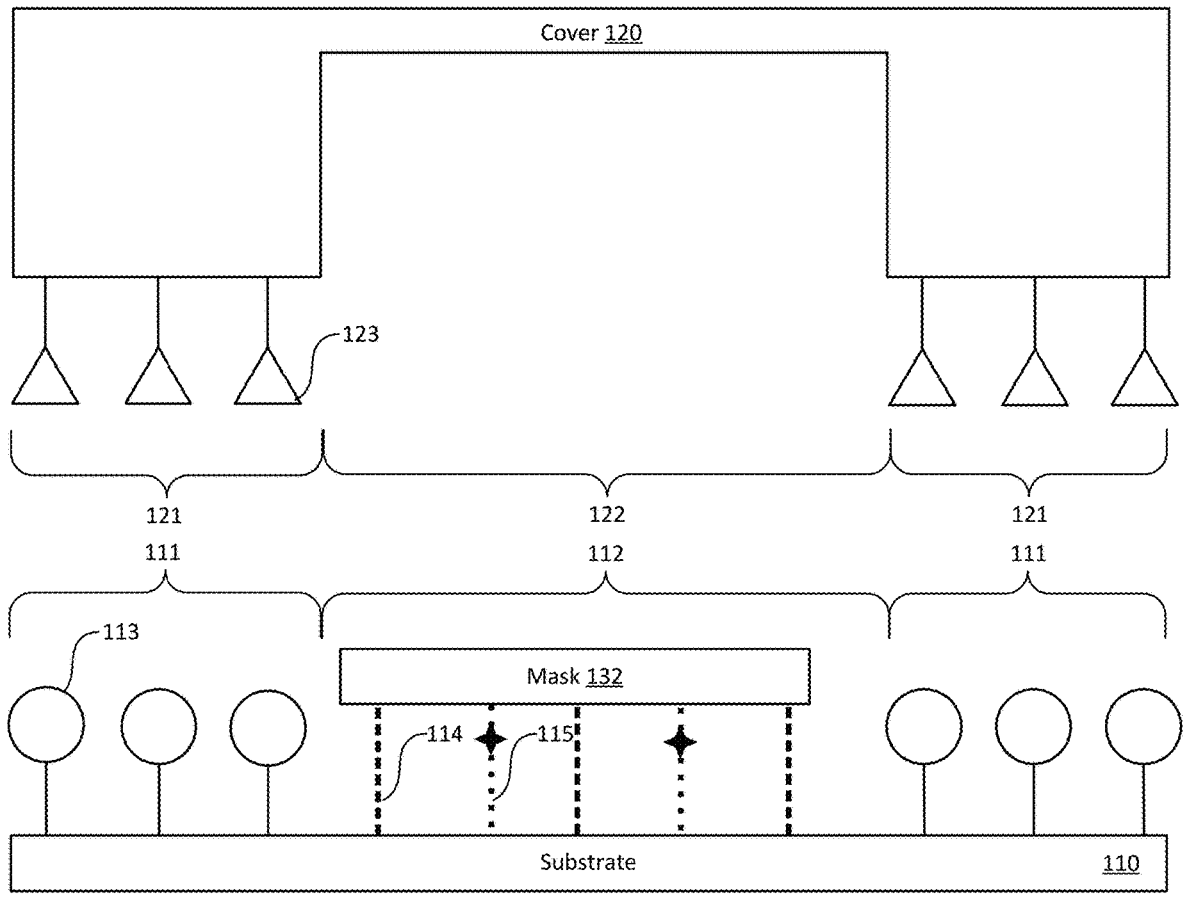
FIGS. 1A-1D schematically illustrate structures and operations in an example process for making a fluidic channel.

Examples provided herein are related to devices including fluidic channels and methods of making the same.

For example, provided herein are methods of forming fluidic channels that include covalently coupling covers to substrates, either directly or through an intervening layer to which the cover and the substrate are both covalently coupled. The covers, substrates, and any intervening layers may include respective moieties that may react with one another without the need for solvents or catalysts. For example, the moieties may include Click chemistry moieties that perform an azide-alkyne [3+2] cyclo-addition reaction with one another. However, it will be appreciated that any suitable chemistry may be used that forms covalent bonds, such as non-Click reactions which are thermally driven (e.g., epoxy-amine reaction). In some examples, other portion(s) of the substrate may be coupled to oligonucleotides, e.g., capture primers such as may be used to amplify target polynucleotides. For example, the cover may be covalently coupled to the substrate so as to suspend a portion of a cover over a portion of the substrate to which oligonucleotides are coupled. The fluidic channel provided by the covalent coupling between the cover and the substrate may be used to flow fluid(s) over the oligonucleotides, e.g., fluids including target polynucleotides, polymerases, nucleotides, reagents, and the like. The covalent coupling between the cover and substrate may be expected to be substantially unreactive with fluid(s) within the fluidic channel. Additionally, or alternatively, such covalent coupling between the cover and substrate may be expected not to fluoresce in such a way that interferes with detection of a desired fluorescent signal. Additionally, or alternatively, such covalent coupling between the cover and substrate may be expected to be more thermally stable than conventional adhesives, and thus may be expected to inhibit leaks or other damage. Accordingly, fluidic devices that include the present fluidic channels may be expected to be particularly robust and useful for handling many different types of fluids.

First, some terms used herein will be briefly explained. Then, some example devices including fluidic channels, and methods of making the same, will be described.

Terms

Unless defined otherwise, all technical and scientific terms used herein have the same meaning as is commonly understood by one of ordinary skill in the art. The use of the term "including" as well as other forms, such as "include," "includes," and "included," is not limiting. The use of the term "having" as well as other forms, such as "have," "has," and "had," is not limiting. As used in this specification, whether in a transitional phrase or in the body of the claim, the terms "comprise(s)" and "comprising" are to be interpreted as having an open-ended meaning. That is, the above terms are to be interpreted synonymously with the phrases "having at least" or "including at least." For example, when used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

The terms "substantially", "approximately", and "about" used throughout this Specification are used to describe and account for small fluctuations, such as due to variations in processing. For example, they can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

As used herein, terms such as "covalently coupled" or "covalently bonded" refer to the forming of a chemical bond that is characterized by the sharing of pairs of electrons between atoms. For example, a covalently coupled molecule refers to a molecule that forms chemical bonds with a substrate, as compared to coupling to the surface via other means, for example, a non-covalent bond such as electrostatic interaction.

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" or "$C_{1-4}$alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

The term "halogen" or "halo," as used herein, means fluorine, chlorine, bromine, or iodine, with fluorine and chlorine being examples.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group may be designated as "$C_{1-4}$ alkyl" or similar designations. By way of example only, "$C_{1-4}$ alkyl" or "$C_{1-4}$alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like.

Groups that include an alkenyl group include optionally substituted alkenyl, cycloalkenyl, and heterocycloalkenyl groups.

As used herein, "alkynyl" refers to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group may be designated as "$C_{2-4}$ alkynyl" or similar designations. By way of example only, "$C_{2-4}$ alkynyl" or "$C_{2-4}$alkynyl" indicates that there are two to four carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

Groups that include an alkynyl group include optionally substituted alkynyl, cycloalkynyl, and heterocycloalkynyl groups.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some examples, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

As used herein, "heterocycle" refers to a cyclic compound which includes atoms of carbon along with another atom (heteroatom), for example nitrogen, oxygen or sulfur. Heterocycles may be aromatic (heteroaryl) or aliphatic. An aliphatic heterocycle may be completely saturated or may contain one or more or two or more double bonds, for example the heterocycle may be a heterocycloalkyl. The heterocycle may include a single heterocyclic ring or multiple heterocyclic rings that are fused.

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some examples, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

As used herein, "cycloalkyl" means a fully saturated carbocyclyl ring or ring system. Examples include cyclopropyl, cyclobutyl, cyclopentyl, and cyclohexyl.

As used herein, "cycloalkenyl" or "cycloalkene" means a carbocyclyl ring or ring system having at least one double bond, wherein no ring in the ring system is aromatic. An example is cyclohexenyl or cyclohexene. Another example is norbornene or norbornenyl.

As used herein, "heterocycloalkenyl" or "heterocycloalkene" means a carbocyclyl ring or ring system with at least one heteroatom in ring backbone, having at least one double bond, wherein no ring in the ring system is aromatic. In some examples, heterocycloalkenyl or heterocycloalkene ring or ring system is 3-membered, 4-membered, 5-membered, 6-membered, 7-membered, 8-membered, 9-membered, or 10-membered.

As used herein, "cycloalkynyl" or "cycloalkyne" means a carbocyclyl ring or ring system having at least one triple bond, wherein no ring in the ring system is aromatic. An example is cyclooctyne. Another example is bicyclononyne. Another example is dibenzocyclooctyne (DBCO).

As used herein, "heterocycloalkynyl" or "heterocycloalkyne" means a carbocyclyl ring or ring system with at least one heteroatom in ring backbone, having at least one triple bond, wherein no ring in the ring system is aromatic. In some examples, heterocycloalkynyl or heterocycloalkyne ring or ring system is 3-membered, 4-membered, 5-membered, 6-membered, 7-membered, 8-membered, 9-membered, or 10-membered.

As used herein, "heterocycloalkyl" means a non-aromatic cyclic ring or ring system containing at least one heteroatom in the ring backbone. Heterocycloalkyls may be joined together in a fused, bridged or spiro-connected fashion. Heterocycloalkyls may have any degree of saturation provided that at least one heterocyclic ring in the ring system is not aromatic. The heterocycloalkyl group may have 3 to 20 ring members (i.e., the number of atoms making up the ring backbone, including carbon atoms and heteroatoms), although the present definition also covers the occurrence of the term "heterocycloalkyl" where no numerical range is designated. The heterocycloalkyl group may also be a medium size heterocycloalkyl having 3 to 10 ring members. The heterocycloalkyl group could also be a heterocycloalkyl having 3 to 6 ring members. The heterocycloalkyl group may be designated as "3-6 membered heterocycloalkyl" or similar designations. In some six membered monocyclic heterocycloalkyls, the heteroatom(s) are selected from one up to three of O, N or S, and in some five membered monocyclic heterocycloalkyls, the heteroatom(s) are selected from one or two heteroatoms selected from O, N, or S. Examples of heterocycloalkyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 2H-1,3-oxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$) alkyl (e.g., —$CF_3$), halo($C_1$-$C_6$alkoxy (e.g., —$OCF_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O). Wherever a group is described as "optionally substituted" that group can be substituted with the above substituents.

Where the compounds disclosed herein have at least one stereocenter, they may exist as individual enantiomers or diastereomers, or as mixtures of such isomers, including racemates. Separation of the individual isomers or selective synthesis of the individual isomers is accomplished by application of various methods which are well known to practitioners in the art. Where compounds disclosed herein are understood to exist in tautomeric forms, all tautomeric forms are included in the scope of the structures depicted. Unless otherwise indicated, all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

As used herein, the term "nucleotide" is intended to mean a molecule that includes a sugar and at least one phosphate group, and in some examples also includes a nucleobase. A nucleotide that lacks a nucleobase may be referred to as "abasic." Nucleotides include deoxyribonucleotides, modified deoxyribonucleotides, ribonucleotides, modified ribonucleotides, peptide nucleotides, modified peptide nucleotides, modified phosphate sugar backbone nucleotides, and mixtures thereof. Examples of nucleotides include adenosine monophosphate (AMP), adenosine diphosphate (ADP), adenosine triphosphate (ATP), thymidine monophosphate (TMP), thymidine diphosphate (TDP), thymidine triphosphate (TTP), cytidine monophosphate (CMP), cytidine diphosphate (CDP), cytidine triphosphate (CTP), guanosine monophosphate (GMP), guanosine diphosphate (GDP), guanosine triphosphate (GTP), uridine monophosphate (UMP), uridine diphosphate (UDP), uridine triphosphate (UTP), deoxyadenosine monophosphate (dAMP), deoxyadenosine diphosphate (dADP), deoxyadenosine triphosphate (dATP), deoxythymidine monophosphate (dTMP), deoxythymidine diphosphate (dTDP), deoxythymidine triphosphate (dTTP), deoxycytidine diphosphate (dCDP), deoxycytidine triphosphate (dCTP), deoxyguanosine monophosphate (dGMP), deoxyguanosine diphosphate (dGDP), deoxyguanosine triphosphate (dGTP), deoxyuridine monophosphate (dUMP), deoxyuridine diphosphate (dUDP), and deoxyuridine triphosphate (dUTP).

As used herein, the term "nucleotide" also is intended to encompass any nucleotide analogue which is a type of nucleotide that includes a modified nucleobase, sugar and/or phosphate moiety compared to naturally occurring nucleotides. Example modified nucleobases include inosine, xathanine, hypoxathanine, isocytosine, isoguanine, 2-aminopurine, 5-methylcytosine, 5-hydroxymethyl cytosine, 2-aminoadenine, 6-methyl adenine, 6-methyl guanine, 2-propyl guanine, 2-propyl adenine, 2-thiouracil, 2-thiothymine, 2-thiocytosine, 15-halouracil, 15-halocytosine, 5-propynyl uracil, 5-propynyl cytosine, 6-azo uracil, 6-azo cytosine, 6-azo thymine, 5-uracil, 4-thiouracil, 8-halo adenine or guanine, 8-amino adenine or guanine, 8-thiol adenine or guanine, 8-thioalkyl adenine or guanine, 8-hydroxyl adenine or guanine, 5-halo substituted uracil or cytosine, 7-methylguanine, 7-methyladenine, 8-azaguanine, 8-azaadenine, 7-deazaguanine, 7-deazaadenine, 3-deazaguanine, 3-deazaadenine or the like. As is known in the art, certain nucleotide analogues cannot become incorporated into a polynucleotide, for example, nucleotide analogues such as adenosine 5'-phosphosulfate. Nucleotides may include any suitable number of phosphates, e.g., three, four, five, six, or more than six phosphates.

As used herein, the term "polynucleotide" refers to a molecule that includes a sequence of nucleotides that are bonded to one another. A polynucleotide is one nonlimiting example of a polymer. Examples of polynucleotides include deoxyribonucleic acid (DNA), ribonucleic acid (RNA), locked nucleic acid (LNA), peptide nucleic acid (PNA), and analogues thereof. A polynucleotide may be a single stranded sequence of nucleotides, such as RNA or single stranded DNA, a double stranded sequence of nucleotides, such as double stranded DNA, DNA that is folded to form a hairpin that is partially single stranded and partially double stranded, double-stranded amalgamations in which there are molecules that are non-covalently coupled to one another (e.g., via reversible hydrogen binding), and/or may include a mixture of a single stranded and double stranded sequences of nucleotides. Double stranded DNA (dsDNA) includes genomic DNA, and PCR and amplification products. Single stranded DNA (ssDNA) can be converted to dsDNA and vice-versa. Polynucleotides may include non-naturally occurring DNA, such as enantiomeric DNA. The precise sequence of nucleotides in a polynucleotide may be known or unknown. The following are examples of polynucleotides: a gene or gene fragment (for example, a probe, primer, expressed sequence tag (EST) or serial analysis of gene expression (SAGE) tag), genomic DNA, genomic DNA fragment, exon, intron, messenger RNA (mRNA), transfer RNA, ribosomal RNA, ribozyme, cDNA, recombinant polynucleotide, synthetic polynucleotide, branched polynucleotide, plasmid, vector, isolated DNA of any sequence, isolated RNA of any sequence, nucleic acid probe, primer or amplified copy of any of the foregoing.

As used herein, the term "target polynucleotide" is intended to mean a polynucleotide that is the object of an analysis or action. The analysis or action includes subjecting the polynucleotide to amplification, sequencing, and/or other procedure. A target polynucleotide may include nucleotide sequences additional to a target sequence to be analyzed. For example, a target polynucleotide may include one or more adapters, including an adapter that functions as a primer binding site, that flank(s) a target polynucleotide sequence that is to be analyzed. A target polynucleotide hybridized to a capture primer may include nucleotides that extend beyond the 5' or 3' end of the capture oligonucleotide in such a way that not all of the target polynucleotide is amenable to extension. In particular examples, target polynucleotides may have different sequences than one another but may have first and second adapters that are the same as one another. The two adapters that may flank a particular target polynucleotide sequence may have the same sequence as one another, or complementary sequences to one another, or the two adapters may have different sequences. Thus, species in a plurality of target polynucleotides may include regions of known sequence that flank regions of unknown sequence that are to be evaluated by, for example, sequencing (e.g., SBS). In some examples, target polynucleotides carry an adapter at a single end, and such adapter may be located at either the 3' end or the 5' end the target polynucleotide. Target polynucleotides may be used without any adapter, in which case a primer binding sequence may come directly from a sequence found in the target polynucleotide.

The terms "polynucleotide" and "oligonucleotide" are used interchangeably herein. The different terms are not intended to denote any particular difference in size, sequence, or other property unless specifically indicated otherwise. For clarity of description the terms may be used to distinguish one species of polynucleotide from another when describing a particular method or composition that includes several polynucleotide species.

As used herein, a "polymerase" is intended to mean an enzyme having an active site that assembles polynucleotides by polymerizing nucleotides into polynucleotides. A polymerase can bind a primed single stranded target polynucleotide, and can sequentially add nucleotides to the growing primer to form a "complementary copy" polynucleotide having a sequence that is complementary to that of the target polynucleotide. Another polymerase, or the same polymerase, then can form a copy of the target nucleotide by forming a complementary copy of that complementary copy polynucleotide. DNA polymerases may bind to the target polynucleotide and then move down the target polynucleotide sequentially adding nucleotides to the free hydroxyl group at the 3' end of a growing polynucleotide strand (growing amplicon). DNA polymerases may synthesize complementary DNA molecules from DNA templates and RNA polymerases may synthesize RNA molecules from DNA templates (transcription). Polymerases may use a short RNA or DNA strand (primer), to begin strand growth. Some polymerases may displace the strand upstream of the site where they are adding bases to a chain. Such polymerases may be said to be strand displacing, meaning they have an activity that removes a complementary strand from a template strand being read by the polymerase. Example polymerases having strand displacing activity include, without limitation, the large fragment of Bst (Bacillus stearothermophilus) polymerase, exo-Klenow polymerase or sequencing grade T7 exo-polymerase. Some polymerases degrade the strand in front of them, effectively replacing it with the growing chain behind (5' exonuclease activity). Some polymerases have an activity that degrades the strand behind them (3' exonuclease activity). Some useful polymerases have been modified, either by mutation or otherwise, to reduce or eliminate 3' and/or 5' exonuclease activity.

As used herein, the term "primer" refers to a polynucleotide to which nucleotides may be added via a free 3' OH group. The primer length may be any suitable number of bases long and may include any suitable combination of natural and non-natural nucleotides. A target polynucleotide may include an "adapter" that hybridizes to (has a sequence that is complementary to) a primer, and may be amplified so as to generate a complementary copy polynucleotide by adding nucleotides to the free 3' OH group of the primer. A "capture primer" refers to a primer that is coupled to a substrate. In some examples, capture primers are P5 and P7 primers that are commercially available from Illumina, Inc. (San Diego, CA). In some examples, primers (such as primers or P5 or P7 primers) include a linker or spacer at the 5' end. Such linker or spacer may be included in order to permit chemical or enzymatic cleavage, or to confer some other desirable property, for example to enable covalent attachment to a substrate, or to act as spacers to position a site of cleavage an optimal distance from the solid support. In certain cases, 10 spacer nucleotides may be positioned between the point of attachment of the P5 or P7 primers to a polymer or a solid support. In some examples, polyT spacers are used, although other nucleotides and combinations thereof can also be used. In one example, the spacer is a 6T to 10T spacer. In some examples, the linkers include cleavable nucleotides including a chemically cleavable functional group such as a vicinal diol or allyl T.

As used herein, the term "amplicon," when used in reference to a polynucleotide, is intended to mean a product of copying the polynucleotide, wherein the product has a nucleotide sequence that is substantially the same as, or is substantially complementary to, at least a portion of the nucleotide sequence of the polynucleotide. "Amplification" and "amplifying" refer to the process of making an amplicon of a polynucleotide. A first amplicon of a target polynucleotide may be a complementary copy. Additional amplicons are copies that are created, after generation of the first amplicon, from the target polynucleotide or from the first amplicon. A subsequent amplicon may have a sequence that is substantially complementary to the target polynucleotide or is substantially identical to the target polynucleotide. It will be understood that a small number of mutations (e.g., due to amplification artifacts) of a polynucleotide may occur when generating an amplicon of that polynucleotide.

As used herein, the term "silane" refers to an organic or inorganic compound containing one or more silicon atoms. A non-limiting example of an inorganic silane compound is $SiH_4$, or halogenated $SiH_4$ where hydrogen is replaced by one or more halogen atoms. A non-limiting example of an organic silane compound is $X-R^C-Si(OR^D)_3$, wherein X is a non-hydrolyzable organic group, such as amino, vinyl, epoxy, methacrylate, sulfur, alkyl, alkenyl, or alkynyl; $R^C$ is a spacer, for example $-(CH_2)_n-$, wherein n is 0 to 1000; each $R^D$ is independently selected from hydrogen, optionally substituted alkyl, optionally substituted alkenyl, optionally substituted alkynyl, optionally substituted carbocyclyl, optionally substituted aryl, optionally substituted 5-10 membered heteroaryl, and optionally substituted 5-10 membered heterocyclyl, as defined herein. In some examples, the silanes may be cross-linked such that the oxygen atom of an $-OR^D$ group of $X-R^C-Si(OR^D)_3$, is attached to the silicon atom of an adjacent organic silane compound, $X-R^C-Si(OR^D)_3$. Furthermore, the silane compounds may be attached to a substrate surface by covalent binding of the $X-R^C-Si(OR^D)_3$ moieties to oxygen atoms on the surface. Thus, in some examples, the silanes described include the following structure:

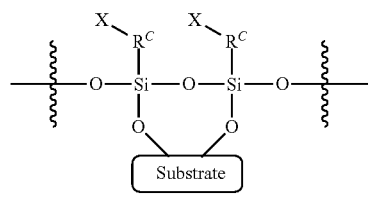

As used herein, the term "silane" can include mixtures of different silane compounds. In some examples, X is a norbornenyl group. In some examples, X is a bicyclononynyl group. In some examples, X is an alkene- or alkyne-containing group. In some examples, X is alkene or alkyne. In some examples, the $R^C$ linker is a $C_{2-6}$alkylene group.

As used herein, the term "substrate" refers to a material that includes a solid support. A substrate may include a polymer that defines the solid support, or that is disposed on the solid support. Example substrate materials may include glass, silica, plastic, quartz, metal, metal oxide, organo-silicate (e.g., polyhedral organic silsesquioxanes (POSS)), polyacrylates, tantalum oxide, complementary metal oxide semiconductor (CMOS), or combinations thereof. An example of POSS can be that described in Kehagias et al., Microelectronic Engineering 86 (2009), pp. 776-778, which is incorporated by reference in its entirety. Illustratively, POSS-containing monomers may be polymerised reaching a gel-point rapidly to furnish a POSS resin (a polymer functionalized to include POSS) on which soft material functionalisation may be performed. In some examples, substrates used in the present application include silica-based substrates, such as glass, fused silica, or other silica-containing material. In some examples, substrates may include silicon, silicon nitride, or silicone hydride. In some examples, substrates used in the present application include plastic materials or components such as polyethylene, polystyrene, poly(vinyl chloride), polypropylene, nylons, polyesters, polycarbonates, and poly(methyl methacrylate). Example plastics materials include poly(methyl methacrylate), polystyrene, cyclic olefin copolymer, and cyclic olefin polymer substrates. In some examples, the substrate is or includes a silica-based material or plastic material or a combination thereof. In particular examples, the substrate has at least one surface comprising glass or a silicon-based polymer. In some examples, the substrates may include a metal. In some such examples, the metal is gold. In some examples, the substrate has at least one surface comprising a metal oxide. In one example, the surface comprises a tantalum oxide or tin oxide. Acrylamides, enones, or acrylates may also be utilized as a substrate material or component. Other substrate materials may include, but are not limited to gallium arsenide, indium phosphide, aluminum, ceramics, polyimide, quartz, resins, polymers and copolymers. In some examples, the substrate and/or the substrate surface may be, or include, quartz. In some other examples, the substrate and/or the substrate surface may be, or include, semiconductor, such as GaAs or ITO. The foregoing lists are intended to be illustrative of, but not limiting to the present application. Substrates may comprise a single material or a plurality of different materials. Substrates may be composites or laminates. In some examples, the substrate comprises an organo-silicate material. Substrates may be flat, round, spherical, rod-shaped, or any other suitable shape. Substrates may be rigid or flexible. In some examples, a substrate is a bead or a flow cell.

In some examples, a substrate includes a patterned surface. A "patterned surface" refers to an arrangement of different regions in or on an exposed layer of a substrate. For example, one or more of the regions may be features where one or more capture primers are present. The features can be separated by interstitial regions where capture primers are not present. In some examples, the pattern may be an x-y format of features that are in rows and columns. In some examples, the pattern may be a repeating arrangement of features and/or interstitial regions. In some examples, the pattern may be a random arrangement of features and/or interstitial regions. In some examples, the substrate includes an array of wells (depressions) in a surface. The wells may be provided by substantially vertical sidewalls. In some examples, the substrate includes an array of posts (protrusions) in a surface. Wells and posts may be fabricated as is generally known in the art using a variety of techniques, including, but not limited to, photolithography, stamping techniques, molding techniques, nano-imprint lithography, and microetching techniques. As will be appreciated by those in the art, the technique used will depend on the composition and shape of the array substrate. Illustratively, posts having diameters between about 50 nm to about 500 nm may be referred to as nanoposts, and may have heights of similar dimension to the diameters.

The features in a patterned surface of a substrate may include an array of features (e.g., wells such as microwells or nanowells, or posts such as nanoposts) on glass, silicon, plastic or other suitable material(s) with patterned, covalently-linked gel such as poly(N-(5-azidoacetamidylpentyl) acrylamide-co-acrylamide) (PAZAM). The process creates gel pads used for sequencing that may be stable over sequencing runs with a large number of cycles. The covalent linking of the polymer to the wells may be helpful for maintaining the gel in the structured features throughout the lifetime of the structured substrate during a variety of uses. However in many examples, the gel need not be covalently linked to the wells. For example, in some conditions silane free acrylamide (SFA) which is not predominantly covalently attached to any part of the structured substrate, may be used as the gel material.

In particular examples, a structured substrate may be made by patterning a suitable material with wells (e.g. microwells or nanowells), coating the patterned material with a gel material (e.g., PAZAM, SFA or chemically modified variants thereof, such as the azidolyzed version of SFA (azido-SFA)) and polishing the surface of the gel coated material, for example via chemical or mechanical polishing, thereby retaining gel in the wells but removing or inactivating substantially all of the gel from the interstitial regions on the surface of the structured substrate between the wells. Primers may be attached to gel material. A solution including a plurality of target polynucleotides (e.g., a fragmented human genome or portion thereof) may then be contacted with the polished substrate such that individual target polynucleotides will seed individual wells via interactions with primers attached to the gel material; however, the target polynucleotides will not occupy the interstitial regions due to absence or inactivity of the gel material. Amplification of the target polynucleotides may be confined to the wells because absence or inactivity of gel in the interstitial regions may inhibit outward migration of the growing cluster. The process is conveniently manufacturable, being scalable and utilizing conventional micro- or nano-fabrication methods.

A patterned substrate may include, for example, wells etched provided in a slide or chip. The pattern of the etchings and geometry of the wells may take on a variety of different shapes and sizes, and such features may be physically or functionally separable from each other. Particularly useful substrates having such structural features include patterned substrates that may select the size of solid particles such as microspheres. An example patterned substrate having these characteristics is the etched substrate used in connection with BEAD ARRAY technology (Illumina, Inc., San Diego, CA). Nano-imprint lithography (NIL) may be used to provide wells.

In some examples, a substrate described herein forms at least part of a flow cell or is located in or coupled to a flow cell. Flow cells may include a flow chamber that is divided into a plurality of lanes or a plurality of sectors. Example flow cells and substrates for manufacture of flow cells that may be used in methods and compositions set forth herein include, but are not limited to, those commercially available from Illumina, Inc. (San Diego, CA).

As used herein, the term "fluidic channel" refers to an elongated, at least partially enclosed structure through which a fluid may flow, e.g., through which a fluid may be directed. A fluidic channel may have a length, a width, and a height. The width and height, together, may define a cross-sectional area of the fluidic channel. The cross-section of the fluidic channel may have any suitable shape, e.g., may be completely curved, partially curved, a completely polygonal, or partially polygonal. Illustratively, the cross-section of the fluidic channel may be circular, oval, square, rectangular, or the like. The fluid may substantially fill the cross-sectional area of the fluidic channel. The fluid may flow along the length of the fluidic channel. A fluidic channel may be formed by a cover coupled to a substrate. A flow cell is a nonlimiting example of a fluidic channel.

As used herein, the term "fluidic device" refers to a device that includes at least one fluidic channel, and optionally may include a plurality of fluidic channels.

As used herein, the term "cover" refers to a substrate that may be coupled to another substrate to form a fluidic channel. As such, a cover may include any of the materials described elsewhere herein that may be included in a substrate. A cover may include the same material(s) as the substrate to which it is coupled, or may include one or more different materials than the substrate to which it is coupled. A cover may be coupled directly to a substrate, or may be coupled to an intervening layer that is coupled to a substrate. Although a region of a cover may be described and illustrated as being "over" a substrate, this is intended only to mean that the cover and the substrate are spaced apart from one another, rather than to imply any particular spatial orientation of the cover relative to the substrate. A cover may include a recess configured such that, when the cover is coupled to the substrate, the recess is spaced apart from the substrate so as to provide a fluidic channel. Conversely, the substrate may include a recess configured such that, when the cover is coupled to the substrate, the recess is spaced apart from the cover so as to provide a fluidic channel.

As used herein, the term "intervening layer" refers to an element that may be coupled to a substrate and to a cover so as to couple the substrate to the cover. An intervening layer may include, or may consist essentially of, a polymer.

As used herein, the term "polymer" refers to a molecule including many repeated subunits or recurring units. Non-limiting examples of polymer structures include linear, branched, or hyper-branched polymers. Non-limiting examples of linear polymers including block copolymers or random/statistical copolymers. Non-limiting examples of branched polymers include star polymers, star-shaped or star-block polymers including both hydrophobic and hydrophilic segments, H-shaped polymers including both hydrophobic and hydrophilic segments, dumbbell shaped polymers, comb polymers, brush polymers, dendronized polymers, ladders, and dendrimers. Polymers may be cross-linked, or lightly cross-linked. Polymers as described herein may be linear, branched, hyper-branched or dendritic. The polymers described herein can also be in the form of polymer nanoparticles. Other examples of polymer architectures include, but not limited to ring block polymers and coil-cycle-coil polymers. Polymers with more than one type of recurring unit can be arranged as block copolymers, random copolymers, or alternating copolymers, or mixtures thereof. The final copolymer structure can be in different architectures, including, for example, random copolymer, block copolymer, comb-shaped polymer or star-shaped polymer architectures. Different classes of polymer backbones include, but are not limited to, polyacrylamides, polyacrylates, polyurethanes, polysiloxanes, silicones, poly-acroleins, polyphosphazenes, polyisocyanates, poly-ols, polysaccharides, polypeptides, and combinations thereof. In some examples, the polymer includes polyacrylamide backbone. In some other examples, the polymer includes polyacrylate backbone. In still some other examples, the polymer includes polyurethane backbone. In still some other examples, the polymer includes polyphosphazene backbone. In still some other examples, the polymer includes a dendrimer backbone. A polymer may include one or more moieties that may react with one or more other moieties to form a covalent bond.

As used herein, the term "adduct" is intended to mean the product of a chemical reaction between two or more molecules, where the product contains all of the atoms of the molecules that were reacted.

As used herein, the term "linker" is intended to mean a molecule or molecules via which one element is attached to another element. For example, a linker may attach a molecule to a substrate. Linkers may be covalent, or may be non-covalent. Nonlimiting examples of covalent linkers include alkyl chains, polyethers, amides, esters, aryl groups, polyaryls, and the like. Nonlimiting examples of noncovalent linkers include host-guest complexation, cyclodextrin/norbornene, adamantane inclusion complexation with β-CD, DNA hybridization interactions, streptavidin/biotin, and the like.

As used herein, the term "mask" is intended to mean a first element that inhibits a second element from chemically reacting.

As used herein, the term "selectively" is intended to mean substantially affecting only the subject(s) of the action that is "selectively" being performed on such subject(s).

Fluidic Devices Including Fluidic Channels, and Methods of Making the Same

As noted above and as described in greater detail below, fluidic devices may include fluidic channels that are formed using covalent coupling between moieties that are covalently coupled to substrates and moieties that are covalently coupled to covers. In some examples, the moieties perform azide-alkyne [3+2] cyclo-addition reactions which may be performed without the use of catalysts or solvents, although it will be appreciated that catalysts and/or solvents, and/or other reactions between moieties, may be used. For example, non-Click reactions which are thermally driven (e.g., epoxy-amine reaction) may be used to covalently couple substrates to covers, either directly or through an intervening layer.

FIGS. 1A-1D schematically illustrate structures and operations in an example process for making a fluidic channel. Referring now to FIG. 1A, substrate 110 may include first region(s) 111 and second region 112. Cover 120 may include first region(s) 121 and second region 122. First region(s) 111 of substrate 110 may be coupled to first moieties 113. First region(s) 121 of cover 120 may be coupled to second moieties 123. First region(s) 121 of cover 120 may be covalently coupled to first region(s) 111 of substrate 110 using first moieties 113 and second moieties 123. The covalent coupling between first region(s) 111 of substrate 110 and first region(s) 121 of cover 120 may suspend second region 122 of cover 120 over second region 112 of substrate 110 to form a fluidic channel.

Figure 1B:
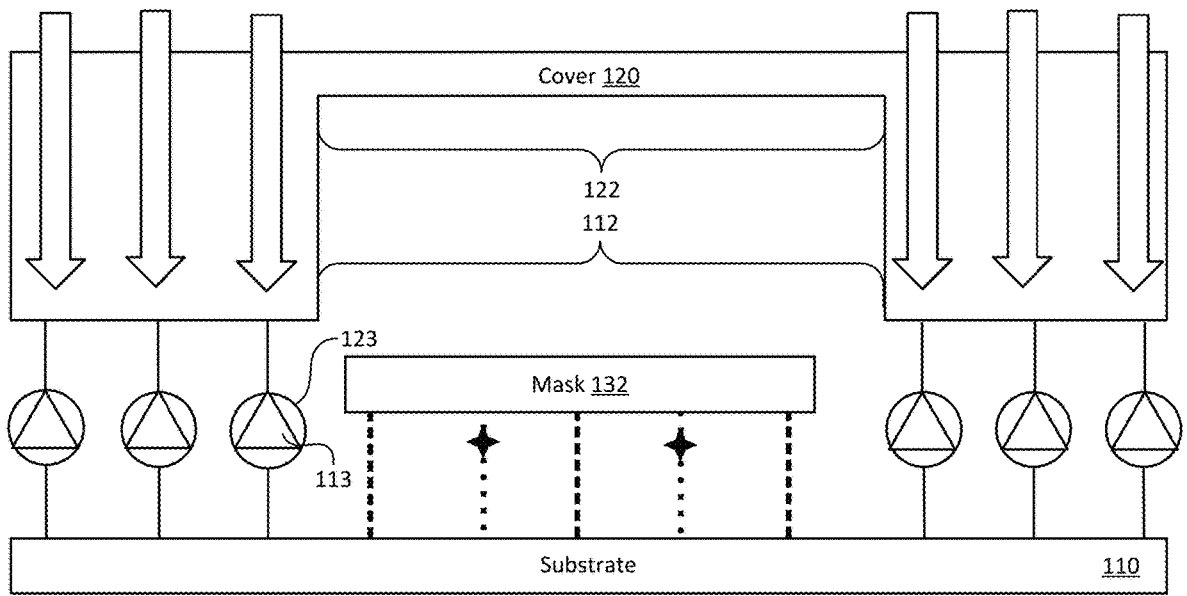
Figure 1C:
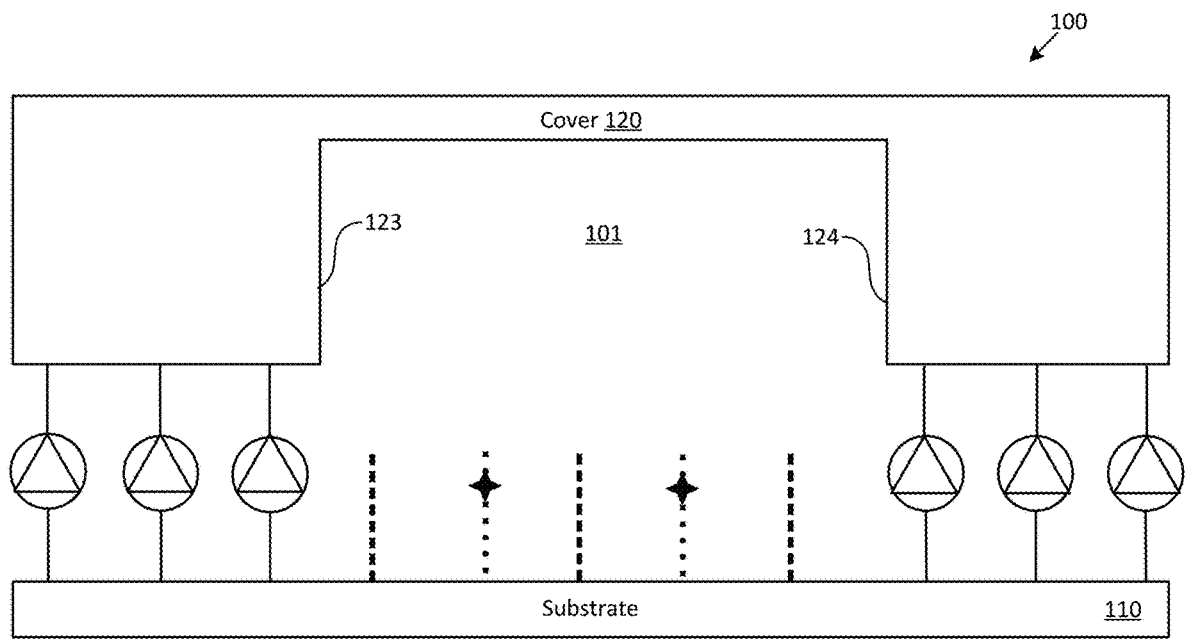
Figure 4A:
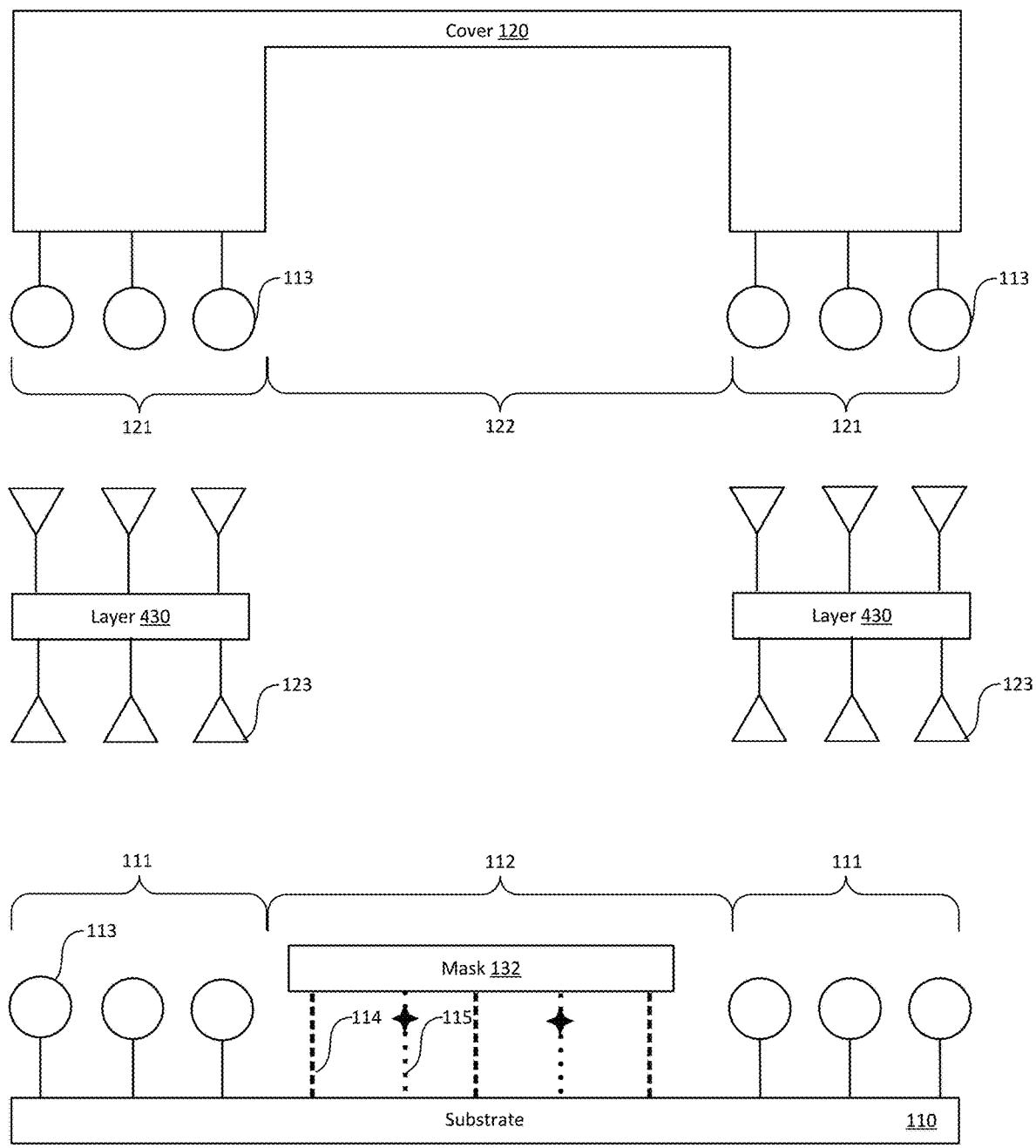
FIGS. 4A-4B schematically illustrate structures and operations in another example process for making a fluidic channel.
Figure 4B:
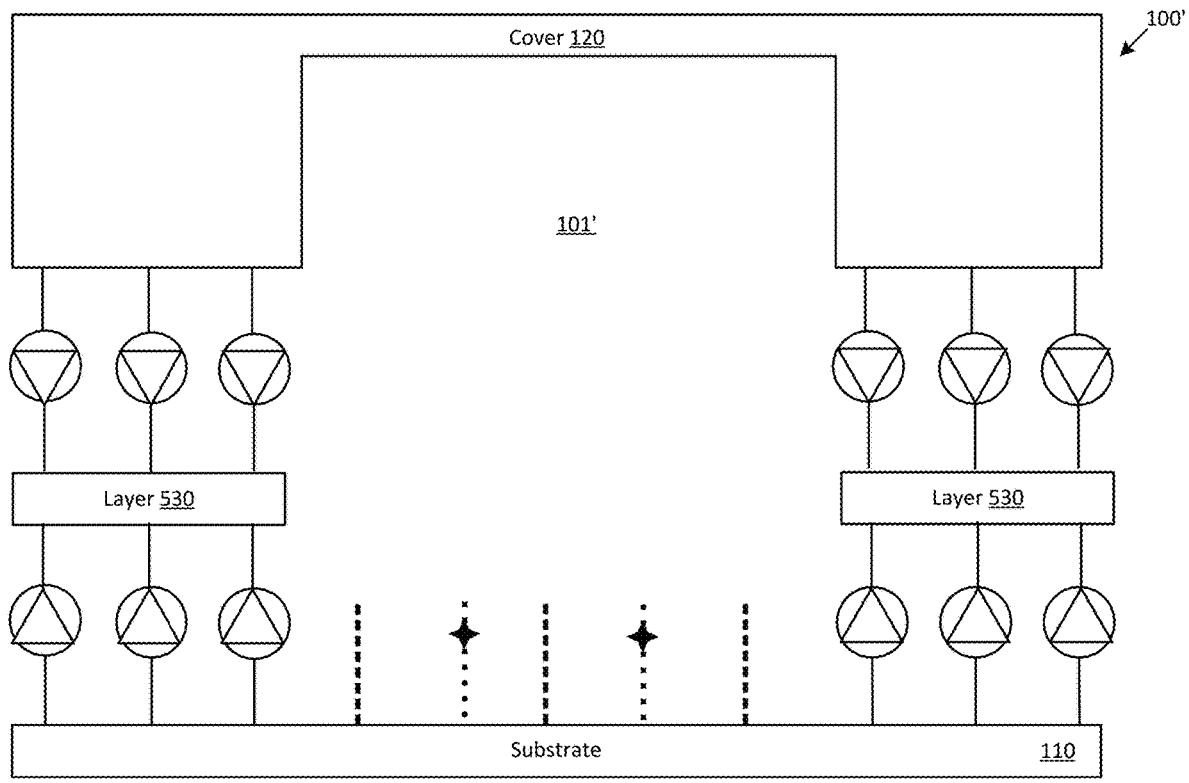

First moieties 113 and second moieties 123 may be used to directly couple first region(s) 111 of substrate 110 to first region(s) 121 of cover 120, e.g., in a manner such as illustrated in FIG. 1B, or alternatively may be used to indirectly couple first region(s) 111 of substrate 110 to first region(s) 121 of cover 120, e.g., via an intervening layer in a manner such as described further below with reference to FIGS. 4A-4B. Illustratively, in the nonlimiting example shown in FIG. 1B, first moieties 113 may directly react with second moieties 123 to covalently couple first region(s) 111 of substrate to second region(s) 121 of cover 120. It will be appreciated that any suitable first moieties 113 may be reacted with any suitable second moieties 123. FIG. 1C illustrates fluidic device 100, including fluidic channel 101, resulting from reactions between first moieties 113 and second moieties 123. Non-limiting examples of moieties 113, 123 are provided below. Example methods and chemical groups that may be used to couple first moieties 113 to substrate 110, and that may be used to couple second moieties 123 to cover 120, are described with reference to FIGS. 5A-5B.

As intended to be suggested by the downward-pointing arrows in FIG. 1B, covalently coupling first region(s) 111 of substrate 110 to first region(s) 121 of cover 120 may include (i) selectively applying heat to the first region of the substrate or the first region of the cover, (ii) applying pressure to the first region of the substrate and the first region of the cover, or (iii) applying both such heat and such pressure. The heat may, for example, increase the rate with at which first region(s) 111 of substrate 110 become covalently bonded to first region(s) 121 of cover 120. Heat may be applied using light, or any other suitable source of heat. Illustratively, the light may include, or may consist essentially of, one or more infrared or near-infrared wavelength(s). For example, a source of collimated light (such as a laser or light emitting diode) may be robotically and/or optically controlled so as to irradiate substantially only first region(s) 111 and/or first regions 121. Pressure may be applied, for example, by retaining substrate 110 in position and robotically or manually pressing cover 120 against substrate 110, or by retaining cover 120 in position and robotically or manually pressing substrate 110 against cover 120.

As illustrated in FIGS. 1A-1C, second region 112 of substrate 110 optionally may include oligonucleotides 114, 115, e.g., capture primers having orthogonal sequences. Any such oligonucleotides 114, 115 optionally may be protected using mask 132 during reactions between moieties 113, 123. Mask 132 may be removed to complete preparation of fluidic device 100 illustrated in FIG. 1C. The fluidic channel provided by second regions 112, 122 may be used to carry fluid(s) across any oligonucleotides 114, 115 that may be coupled to the second region of the substrate. Such fluid(s) may, for example, include a target polynucleotide to be amplified using oligonucleotides 114, 115, and a polymerase and nucleotides for use during such amplification. Example methods for coupling oligonucleotides 114, 115 to second region 112 of substrate 110, in a manner that is compatible with coupling substrate 110 to cover 120, are described with reference to FIGS. 2A-2E, 3A-3E, and 7A-7E. However, it will be appreciated that any other element(s) may be coupled to second region 112 of substrate 110 and/or to any other surfaces within device 100, e.g., to second region 122 of cover 120 and/or to sidewalls 123, 124 coupling first region(s) 121 of cover 120 to second region 122 of the cover.

In the nonlimiting example illustrated in FIG. 1C, second region 122 of cover 120 may be recessed relative to first region(s) 121 and may be coupled to first region(s) via sidewalls 123, 124, while second region 112 of substrate 110 may be substantially planar with first region(s) 111 (FIG. 1A). However, it will be appreciated that in other examples (not specifically illustrated), second region 112 of substrate 110 instead may be recessed relative to first region(s) 111 via similar sidewalls, while second region 122 of cover 120 may be substantially planar with first region(s) 121. In still other examples (not specifically illustrated), second region 112 of substrate 110 is recessed relative to first region(s) 111 via similar sidewalls and second region 122 of cover 120 is recessed relative to first region(s) 121 via similar sidewalls. In any such configuration, the recess or recesses and sidewalls together may provide a space that at least partially encloses second regions 112, 122 when first regions 111, 121 are directly or indirectly coupled to one another in a manner such as provided herein. Such space may provide fluidic channel 101 that may be used to carry fluids across second region 112 of substrate 110. Second region 122 of cover 120 may be separated from second region 112 of substrate 110 by any suitable distance, e.g., by between about 1 μm and about 1 cm, e.g., by between about 1 μm and about 500 μm, or by between about 10 μm and about 100 μm. Sidewalls 123, 124 may be separated from one another by any suitable distance, e.g., by between about 1 μm and about 1 cm, e.g., by between about 1 μm and about 500 μm, or by between about 10 μm and about 100 μm.

Figure 1D:
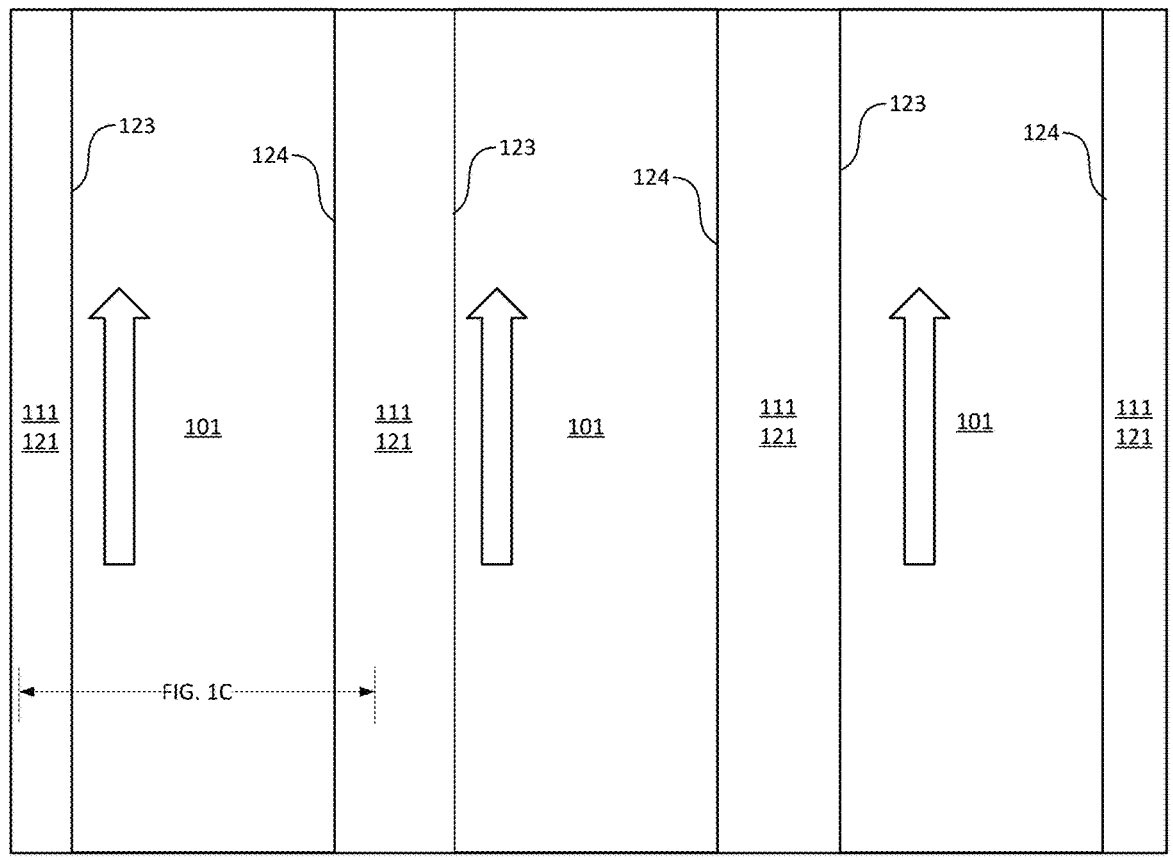

In some examples, a plurality of such recesses and sidewalls are provided in substrate 110 and/or cover 120 so as to form a plurality of fluidic channels 101, e.g., a plurality of flow cells. For example, FIG. 1D illustrates a plan view of an assembly between substrate 110 and cover 120 that includes a plurality of such fluidic channels 101 through which fluid independently may be flowed in a manner such as intended to be suggested by the upward-pointing arrows. Fluidic device 100 illustrated in FIG. 1C may illustrate the cross-section designated "FIG. 1C" in FIG. 1D. However, it will be appreciated that fluidic device 100 illustrated in FIG. 1C need not necessarily be part of an assembly such as illustrated in FIG. 1D.

In some examples, a reaction between first moiety 113 and second moiety 123 such as illustrated in FIG. 1B includes an azide-alkyne [3+2] cyclo-addition, which may be referred to as a Huisgen cyclo-addition. Accordingly, first region(s) 111 may be covalently coupled to first region(s) 121 via the products of such azide-alkyne [3+2] cyclo-addition reactions. In some examples, one of first moiety 113 and second moiety 123 may include azide ($N_3$), and the other of first moiety 113 and second moiety 123 may include a dibenzocyclooctyne (DBCO) having the structure:

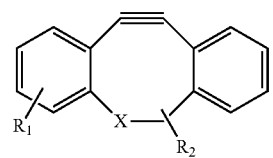

wherein one of $R_1$ and $R_2$ is H and the other is a linkage to substrate 110 (if first moiety 113 includes the DBCO) or to cover 120 (if second moiety 123 includes the DBCO); and wherein X is $CH_2$, O, S, or NH if $R_2$ is not directly coupled to X, or wherein X is CH or N if $R_2$ is directly coupled to X. The azide may be coupled to substrate 110 (if first moiety 113 includes the azide) or to cover 120 (if second moiety 123 includes the azide) via a suitable linkage, such as alkyl. The azide may react with the dibenzocyclooctyne to form a cycloadduct having the structure:

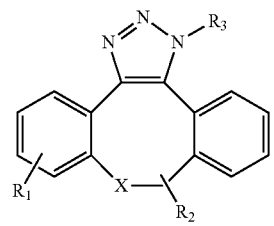

where $R_3$ is a linkage to substrate 110 (if second moiety 123 includes the DBCO) or to cover 120 (if first moiety 113 includes the DBCO). Such reaction, or any other azide-alkyne [3+2] cyclo-addition reaction, optionally may be performed without the use of solvent and/or catalyst. Additionally, or alternatively, the azide-alkyne [3+2] cyclo-addition reaction optionally may be promoted using heat (e.g., from light) and/or pressure in a manner such as described with reference to FIG. 1B.

It will be appreciated that the DBCO represents a non-limiting example of an alkyne that may be used in an azide-alkyne [3+2] cyclo-addition reaction between first moieties 113 and second moieties 123. It will also be appreciated that azide-alkyne [3+2] cyclo-addition reactions represent a non-limiting example of a suitable reaction between first moieties 113 and second moieties 123 to covalently couple first region(s) 111 of substrate 110 to first region(s) 121 of cover 120. Other example alkynes that may be used in an azide-alkyne [3+2] cyclo-addition reaction between first moieties 113 and second moieties 123 include other strained cyclooctynes such as bicyclononyne (BCN) or a derivative thereof, difluorocyclooctyne (DIFO) or a derivative thereof, dibenzocyclooctyne (DIBO) or a derivative thereof, and the like. Some nonlimiting examples of strained cyclooctynes that may be used in an azide-alkyne [3+2] cyclo-addition reaction between first moieties 113 and second moieties 123 include the following, in which R represents a connection to the substrate or cover:

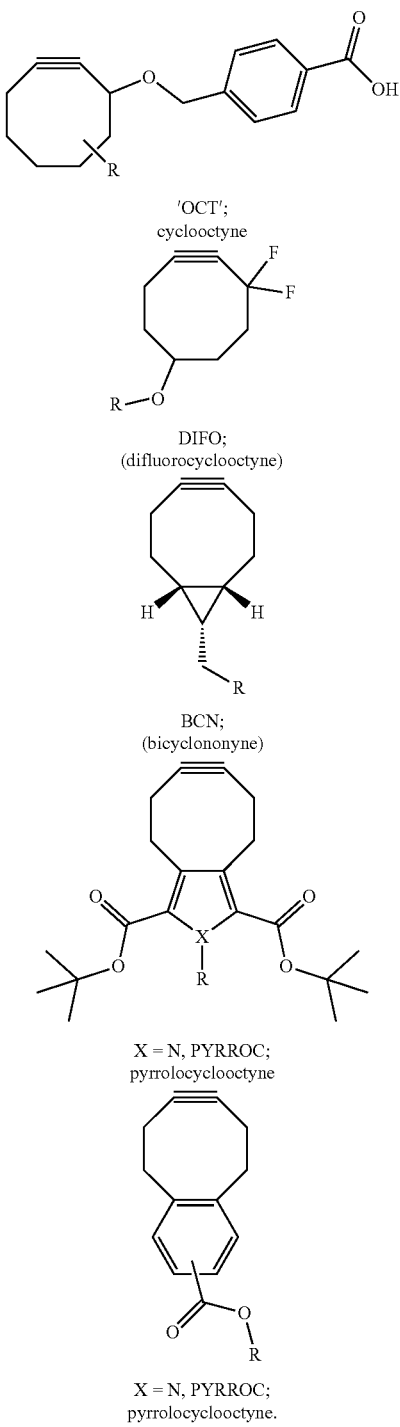

'OCT';
cyclooctyne

DIFO;
(difluorocyclooctyne)

BCN;
(bicyclononyne)

X = N, PYRROC;
pyrrolocyclooctyne

X = N, PYRROC;
pyrrolocyclooctyne.

For further details regarding example reactions between cycloalkynes and azides that may be adapted for use in the present devices and methods, see Dommerholt et al., "Strain-promoted 1,3-dipolar cycloaddition of cycloalkynes and organic azides," Top. Curr. Chem. (Z) 374: 16, 20 pages (2016), the entire contents of which are incorporated by reference herein. However, any surface-bound reactants that form bonds through cycloaddition reactions may be used, such as aryl azides and pentafluoro alkynes. It will also be appreciated that surface-bound reactants that form bonds through other types of addition reactions, such as the thermally driven reaction of a primary amine with an epoxy group.

Figure 2A:
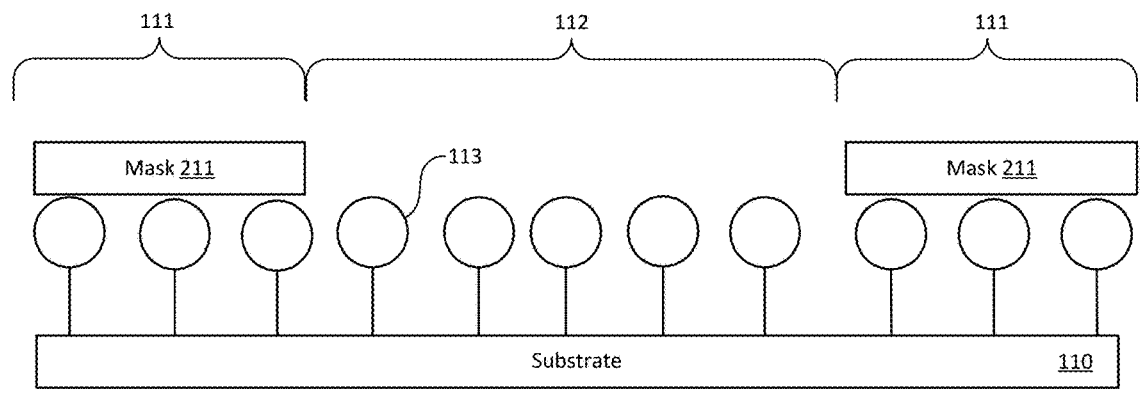
FIGS. 2A-2E schematically illustrate structures and operations in an example process for providing oligonucleotides within a fluidic channel.
Figure 2B:
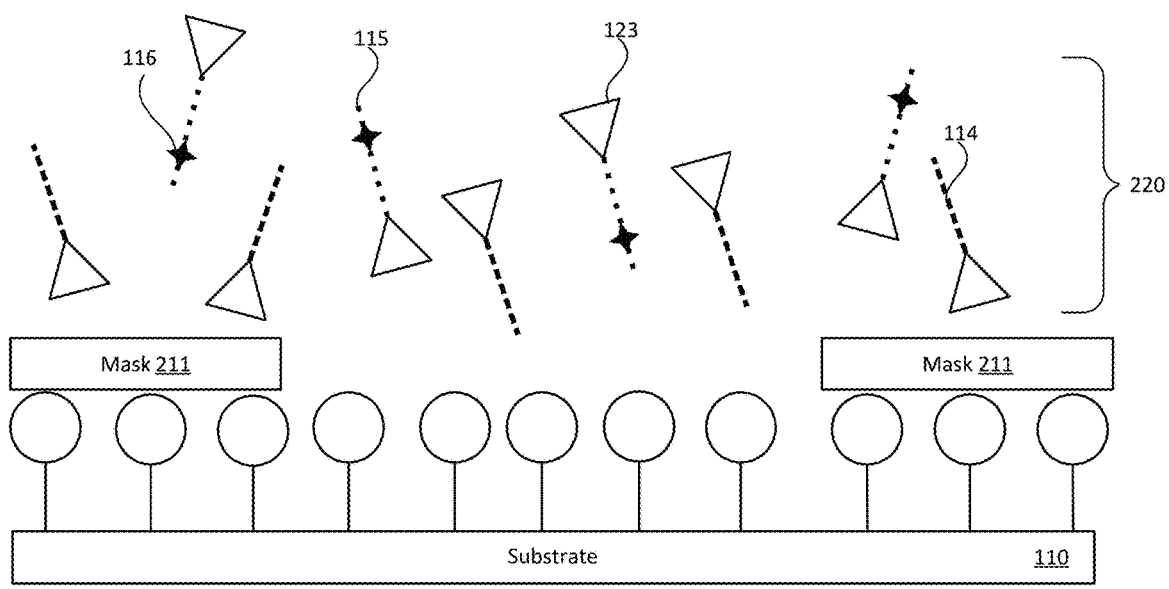
Figure 2C:
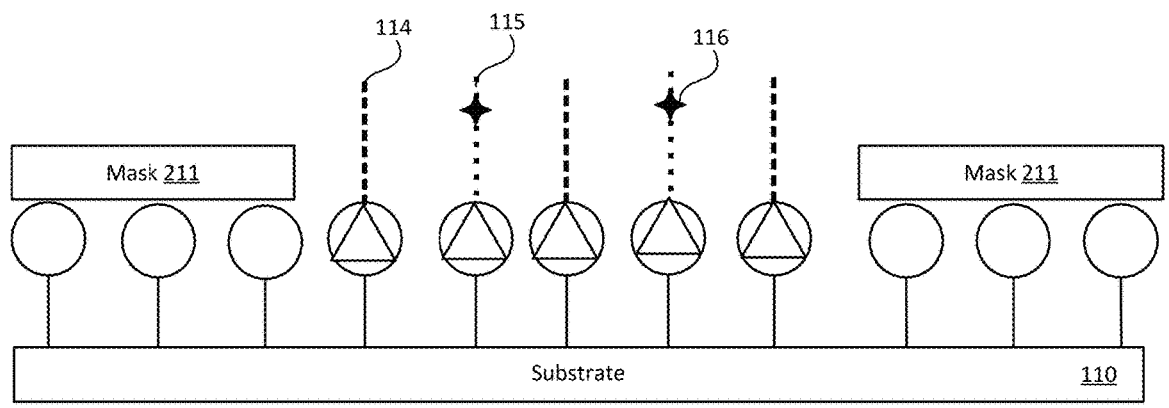
Figure 2D:
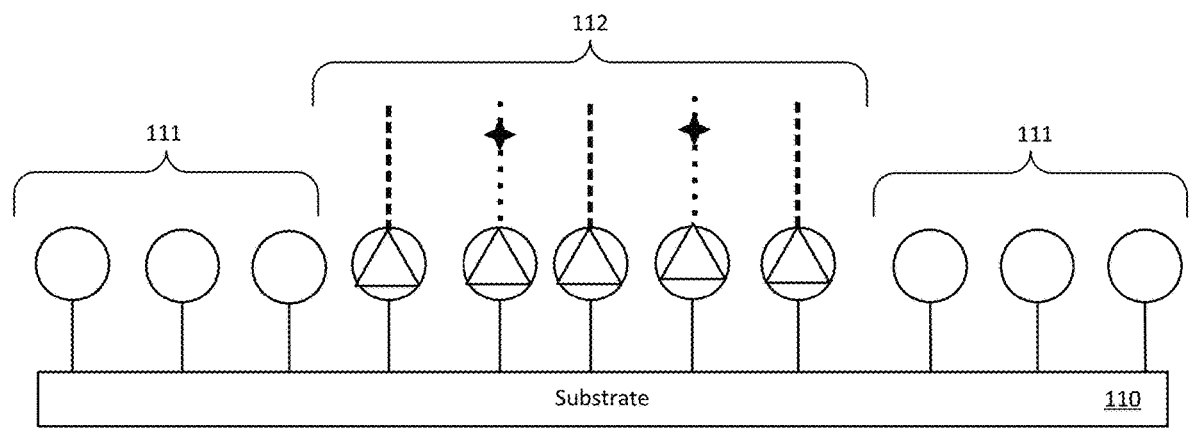
Figure 2E:
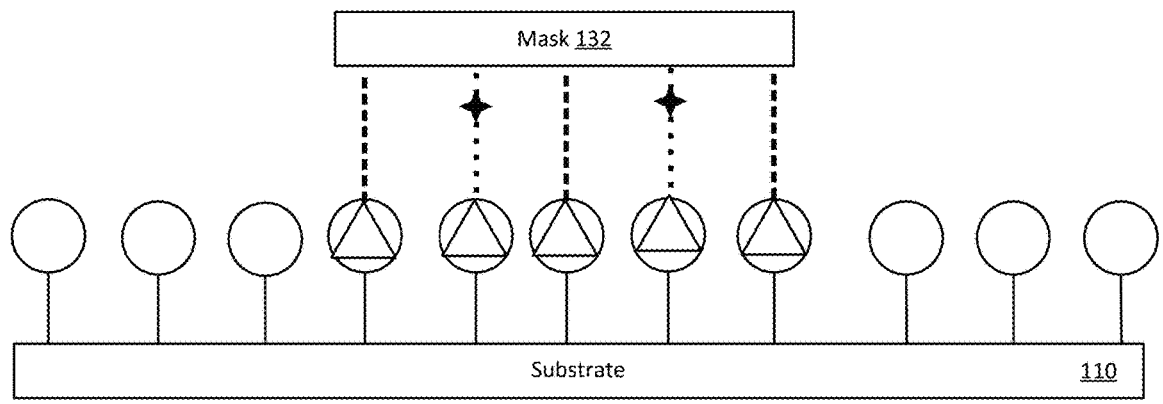

As described above with reference to FIGS. 1A-1C, oligonucleotides 114, 115 may be coupled to second region 112 of substrate 110, e.g., in such a manner as to be contacted by a fluid flowing through fluidic channel 101. Such oligonucleotides may be coupled to second region 112 in any suitable manner and at any suitable time relative to the coupling of substrate 110 to cover 120. FIGS. 2A-2E schematically illustrate structures and operations in an example process for providing oligonucleotides within a fluidic channel. Referring now to FIG. 2A, first region(s) 111 and second region 112 of substrate 110 may be coupled to first moieties 113. So as to inhibit premature reaction of the first moieties 113 within first region(s) 111 of substrate 110, the first region(s) 111 may be protected using mask 211, such as a partially opaque material that is patterned in any suitable manner, e.g., using photolithography, spray coating with a stencil, inkjet printing, aerosol printing, or the like. In one nonlimiting example, mask 211 includes a photolithographically patterned photoresist. As illustrated in FIG. 2B, substrate 110 then may be contacted with fluid 220 including oligonucleotides 114, 115 which are respectively coupled to second moieties 123. Optionally, oligonucleotides 115 include respective excision moieties 116, such as 8-oxo-G, which may be cleaved under suitable conditions such as UV light, chemistry, enzyme, or the like. As illustrated in FIG. 2C, second moieties 123 coupled to respective oligonucleotides 114, 115 may react with moieties 113 within second region 112, thus covalently coupling the oligonucleotides to second region 112. Mask 211 then suitably may be removed in a manner such as illustrated in FIG. 2D. Mask 132, such as a photolithographically patterned coating, then may be applied over the oligonucleotides 114, 115 in second region 112 in a manner such as illustrated in FIG. 2E, so as to protect the oligonucleotides before first region(s) 111 of substrate 110 are covalently coupled to first region(s) 121 of cover 120. In a manner such as described with reference to FIG. 1C, mask 132 may be removed after first region(s) 111 of substrate 110 are covalently coupled to first region(s) 121 of cover 120.

Figure 3A:
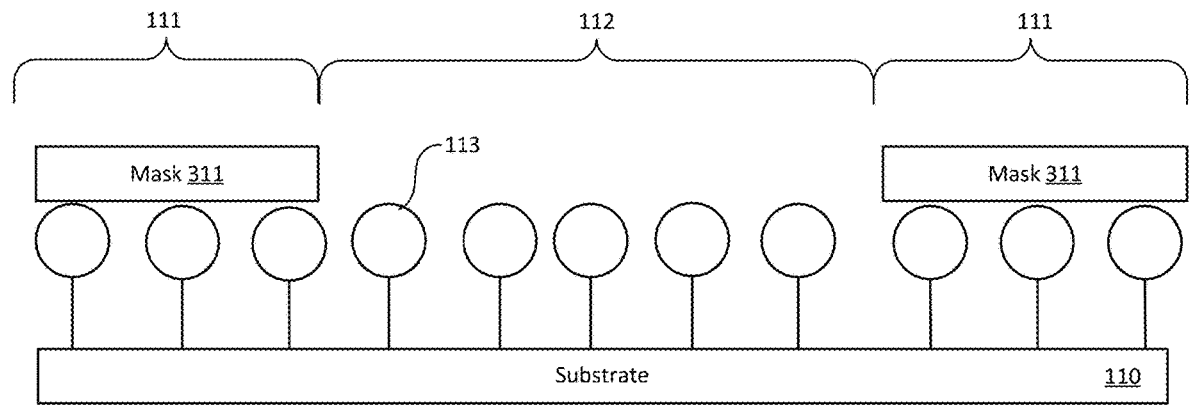
FIGS. 3A-3E schematically illustrate structures and operations in another example process for providing oligonucleotides within a fluidic channel.
Figure 3B:
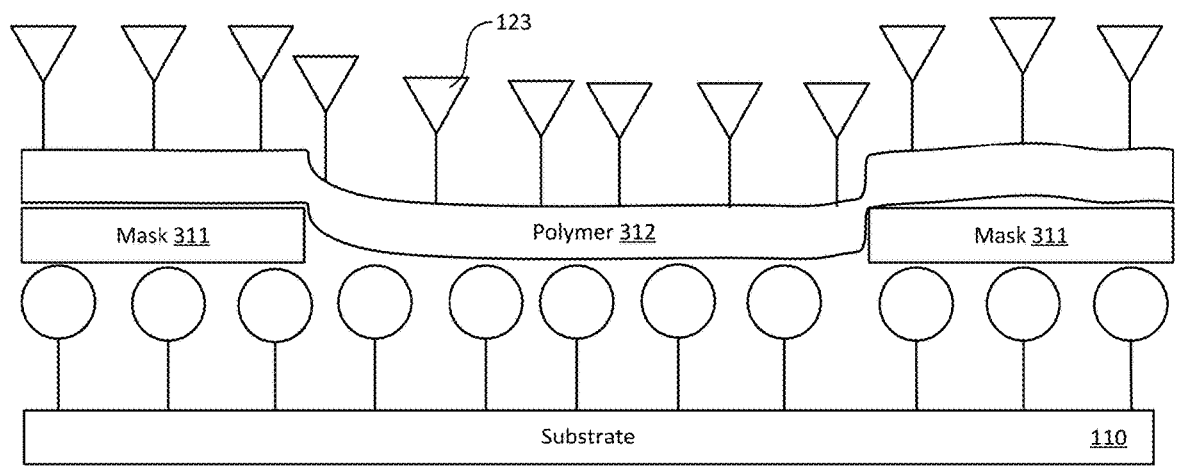

It will be appreciated that second region 112 of substrate 110 may be coupled to moieties other than first moieties 113. For example, FIGS. 3A-3E schematically illustrate structures and operations in another example process for providing oligonucleotides within a fluidic channel. In examples such as described with reference to FIGS. 3A-3E, second region 112 of substrate 110 instead may be coupled to second moieties 123 that are used to couple oligonucleotides to the second region of the substrate. Referring now to FIG. 3A, first region(s) 111 and second region 112 of substrate 110 may be coupled to first moieties 113. So as to inhibit premature reaction of the first moieties 113 within first region(s) 111 of substrate 110, the first region(s) 111 may be protected using mask 311, such as a photolithographically patterned photoresist or other patterned material such as described with reference to mask 211 illustrated in FIGS. 2A-2C. As illustrated in FIG. 3B, polymer 312 may be disposed over, and in contact with, mask 311 in first region(s) 111 and moieties 113 in second region 112. Polymer 312 may include second moieties 123. Although not specifically illustrated in FIG. 3B, it will be appreciated that second moieties 123 of polymer 312 may react with first moieties 113 in region 112, thus covalently coupling the polymer to region 112 of substrate 110. Such reaction may be performed at any suitable time, e.g., when or shortly after polymer 312 is disposed over moieties 113, or after substrate 110 is coupled to cover 120. In one nonlimiting example, polymer 312 may include PAZAM including azide moieties 123, and moieties 113 coupled to substrate 110 may include DBCO moieties that react with the azide moieties to form covalent bonds. In another nonlimiting example, substrate 110 may include PAZAM that is deposited on a solid support and includes azide moieties 113, and polymer 312 may include DBCO moieties 123 that react with the azide moieties to form covalent bonds.

Figure 3C:
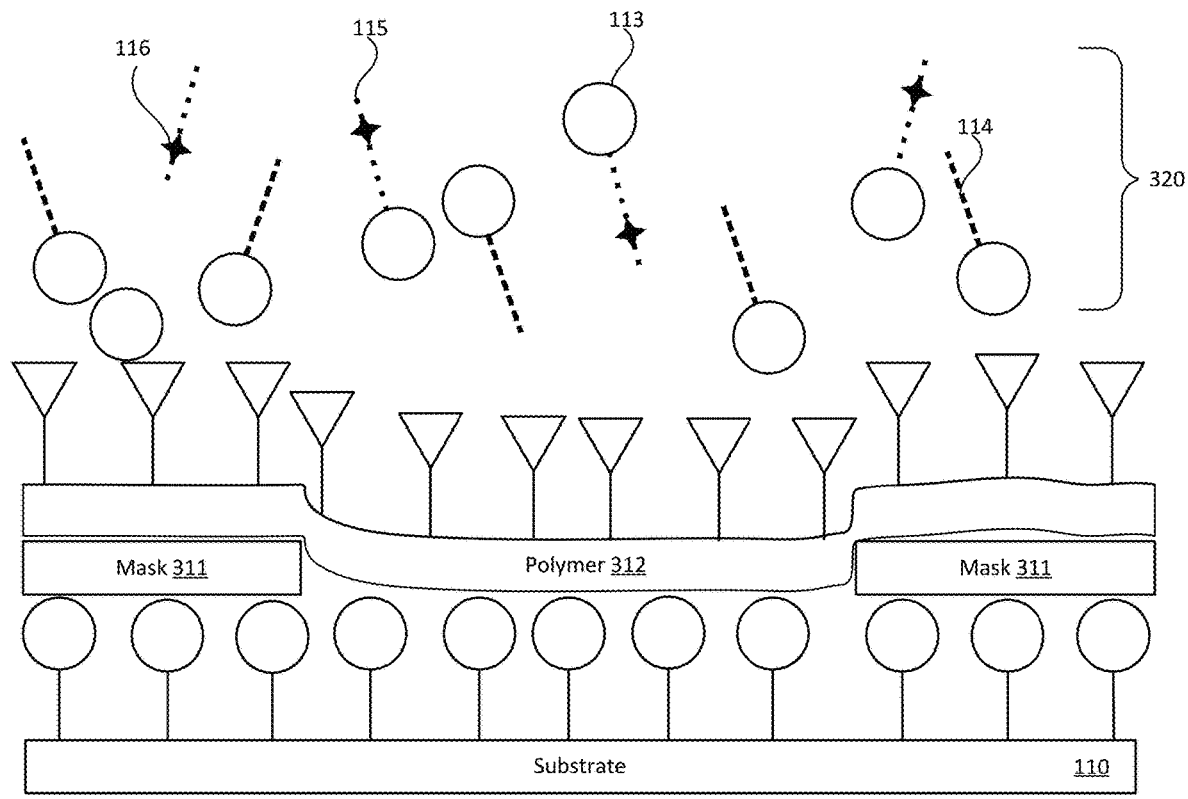
Figure 3D:
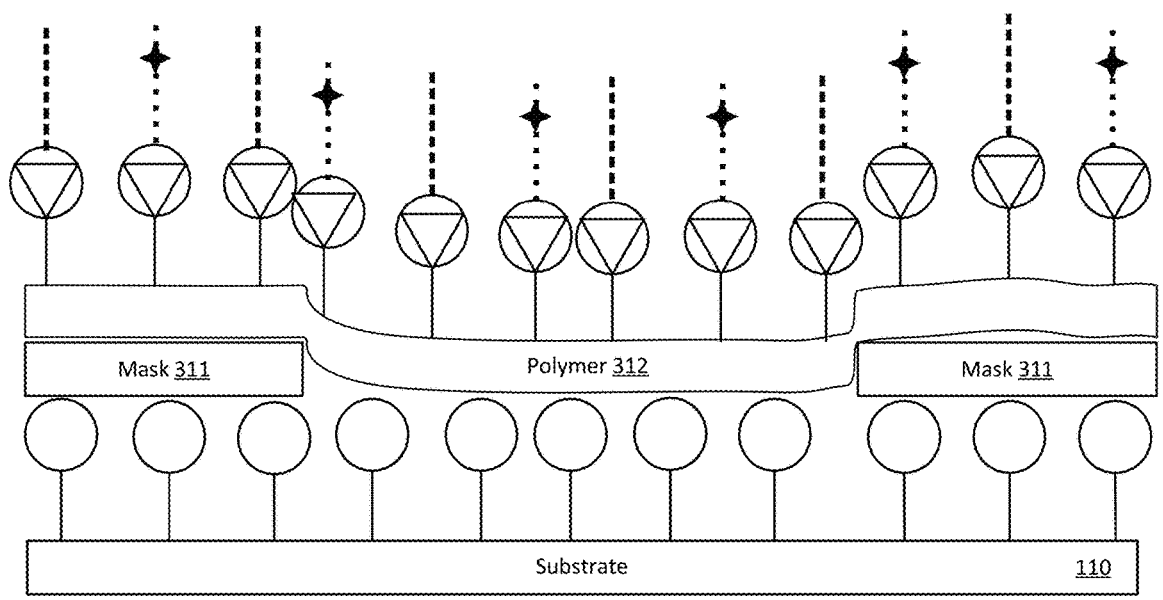
Figure 3E:
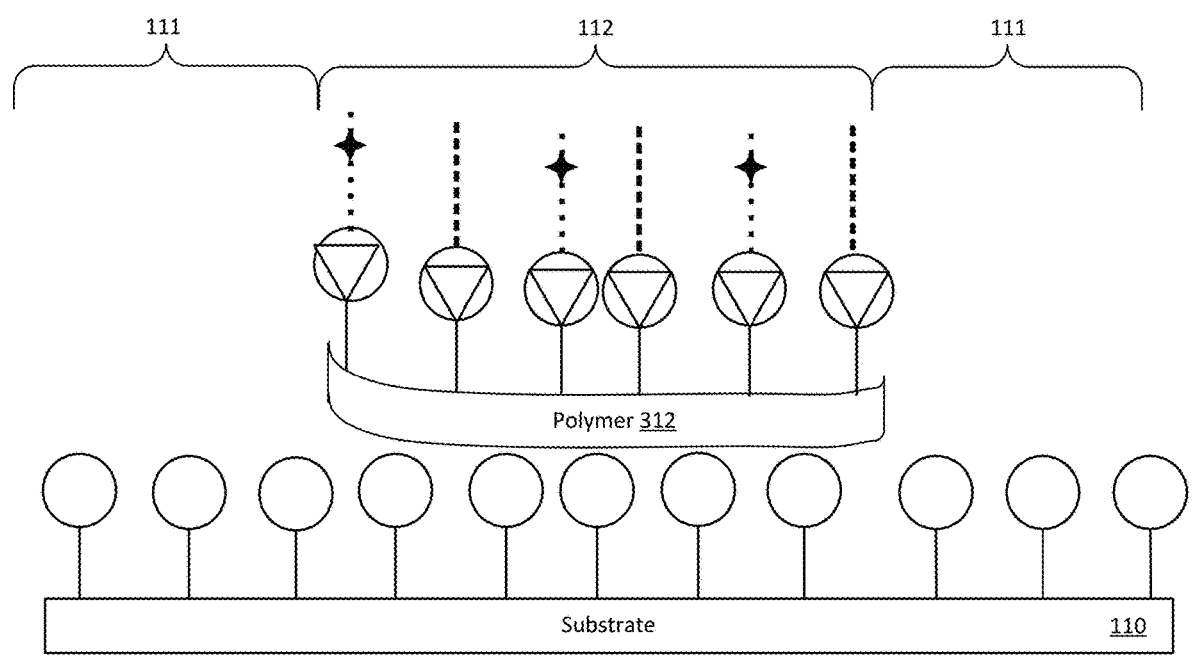

In a manner such as illustrated in FIG. 3C, substrate 110 then may be contacted with fluid 320 including oligonucleotides 114, 115 which are respectively coupled to first moieties 113. Optionally, oligonucleotides 115 include respective excision moieties 116, such as 8-oxo-G, which may be cleaved under suitable conditions such as UV light, chemistry, enzyme, or the like. As illustrated in FIG. 3D, first moieties 113 coupled to respective oligonucleotides 114, 115 may react with second moieties 123 of polymer 312, thus coupling the oligonucleotides to second region 112. Mask 311 then suitably may be removed in a manner such as illustrated in FIG. 3E, which may remove any portions of polymer 312 disposed on such mask. Mask 132 then may be applied over the oligonucleotides 114, 115 in second region 112 in a manner such as described with reference to FIG. 2E, so as to protect the oligonucleotides before first region(s) 111 of substrate 110 are covalently coupled to first region(s) 121 of cover 120. In a manner such as described with reference to FIG. 1C, mask 132 may be removed after first region(s) 111 of substrate 110 are covalently coupled to first region(s) 121 of cover 120.

Figure 7A:
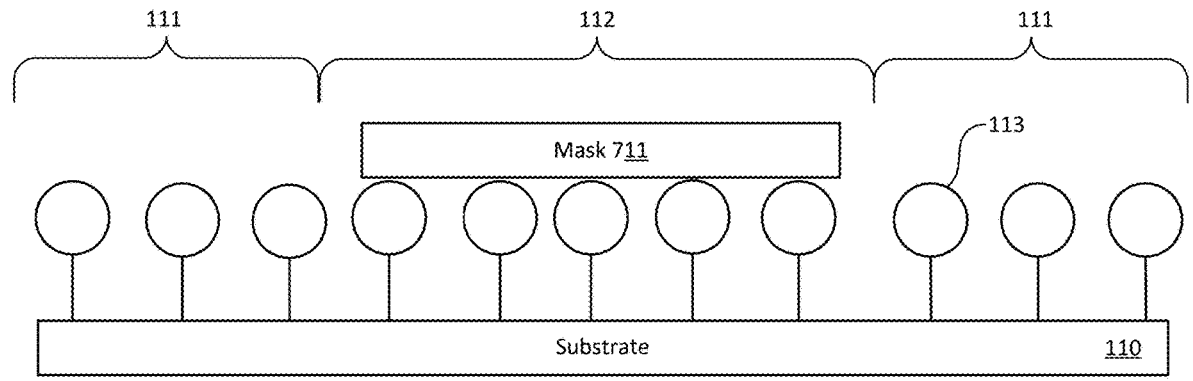
FIGS. 7A-7G schematically illustrate structures and operations in another example process for making a fluidic channel.

Although examples such as described with reference to FIGS. 2A-2E and 3A-3E include coupling oligonucleotides 114, 115 to second region 112 of substrate 110 before first region(s) 111 of the substrate are coupled to first region(s) 121 of the cover, it will be appreciated that the oligonucleotides instead may be coupled to the second region of the substrate after the first region of the substrate is coupled to the first region of the cover. For example, second region 112 of substrate 110 may be coupled to moieties that, after first region(s) 111, 121 are coupled to one another, may be contacted with a fluid that includes oligonucleotides coupled to moieties which may react with the moieties within second region 112. Illustratively, FIGS. 7A-7G schematically illustrate structures and operations in another example process for making a fluidic channel. Referring now to FIG. 7A, first region(s) 111 and second region 112 of substrate 110 may be coupled to first moieties 113. So as to inhibit premature reaction of the first moieties 113 within second region 112 of substrate 110, second region 112 may be protected using mask 711, such as a photolithographically patterned photoresist or other patterned material such as described with reference to mask 211 illustrated in FIGS. 2A-2C.

Figure 7B:
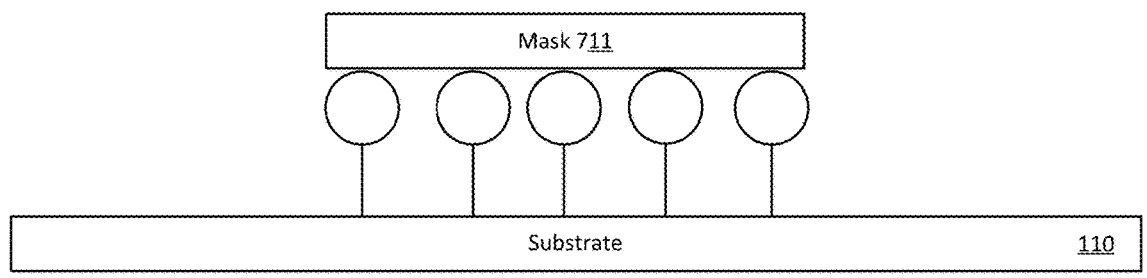
Figure 7C:
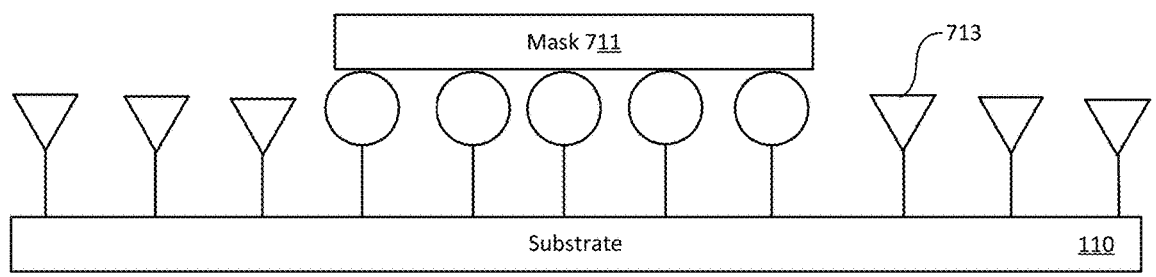
Figure 7D:
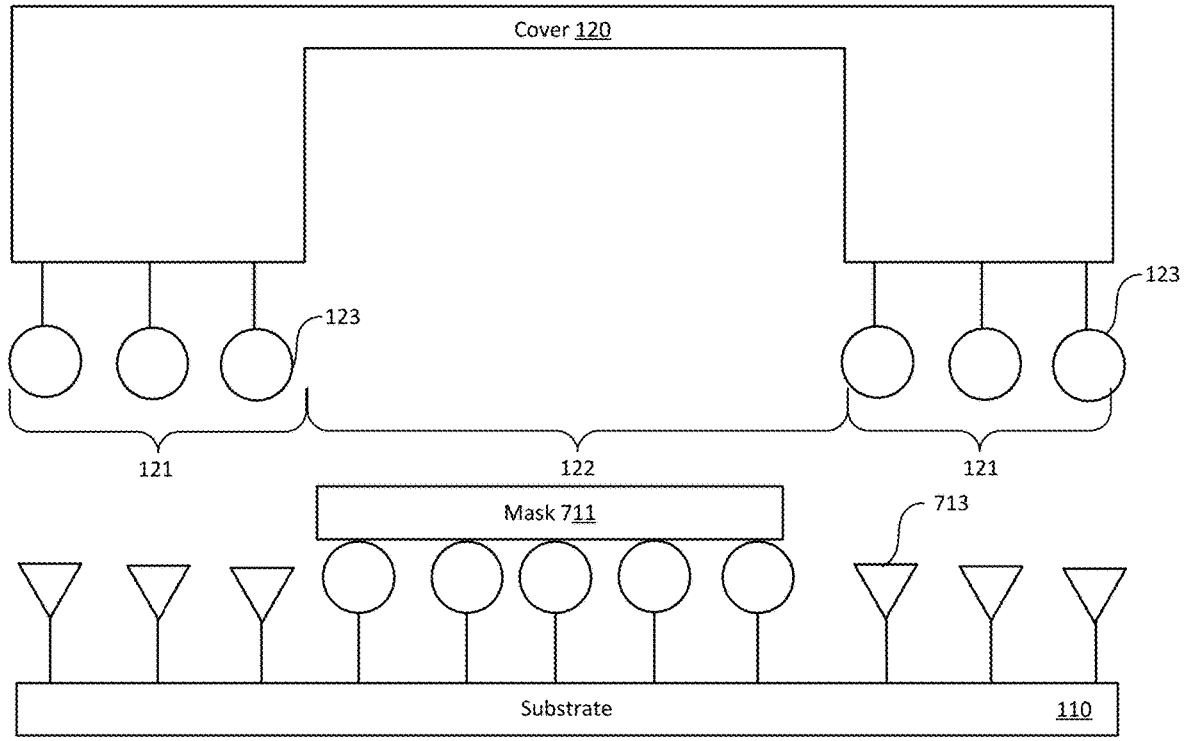
Figure 7E:
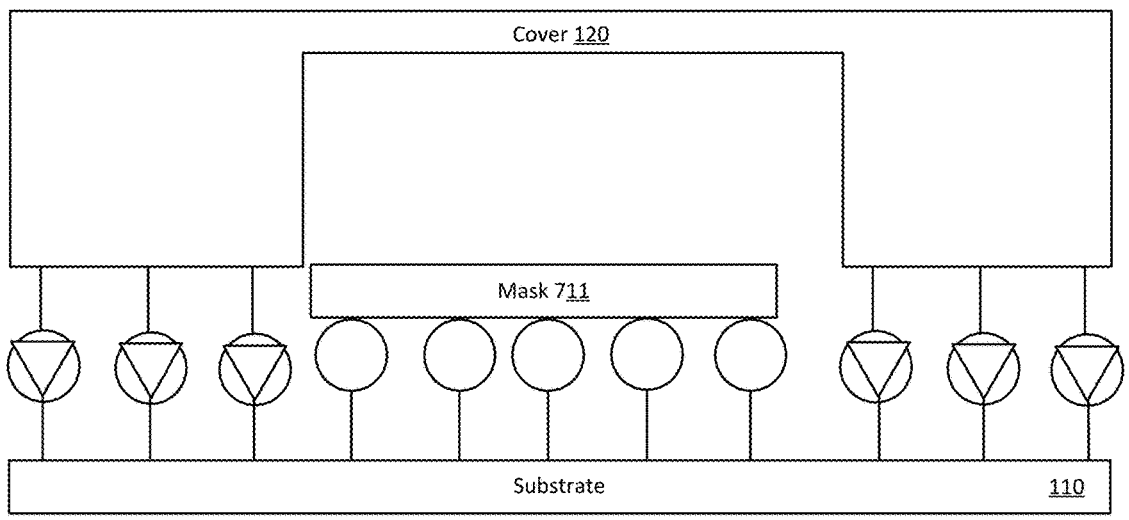
Figure 7F:
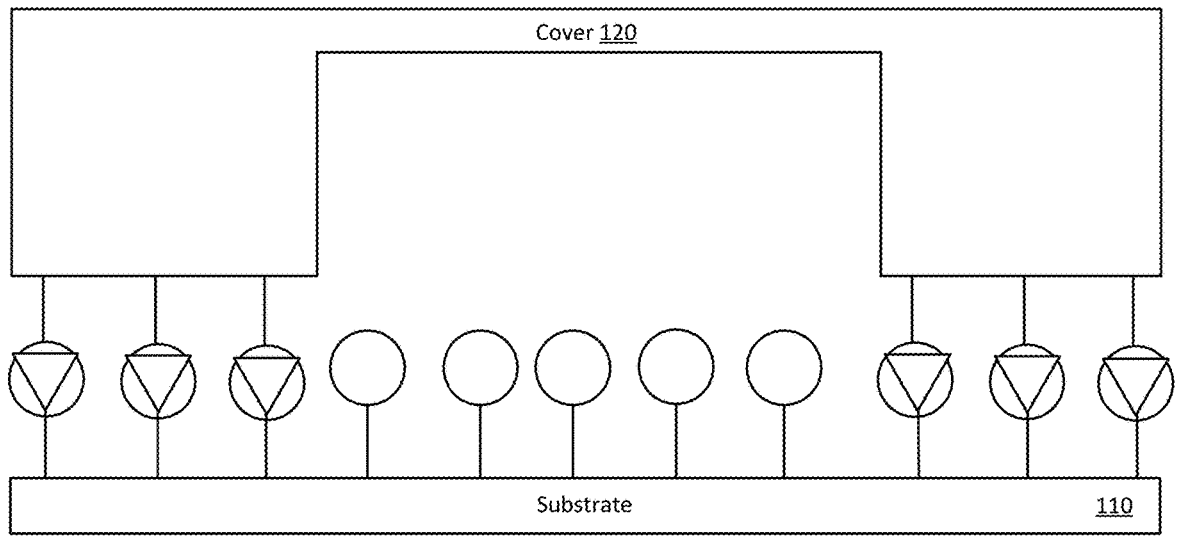
Figure 7G:
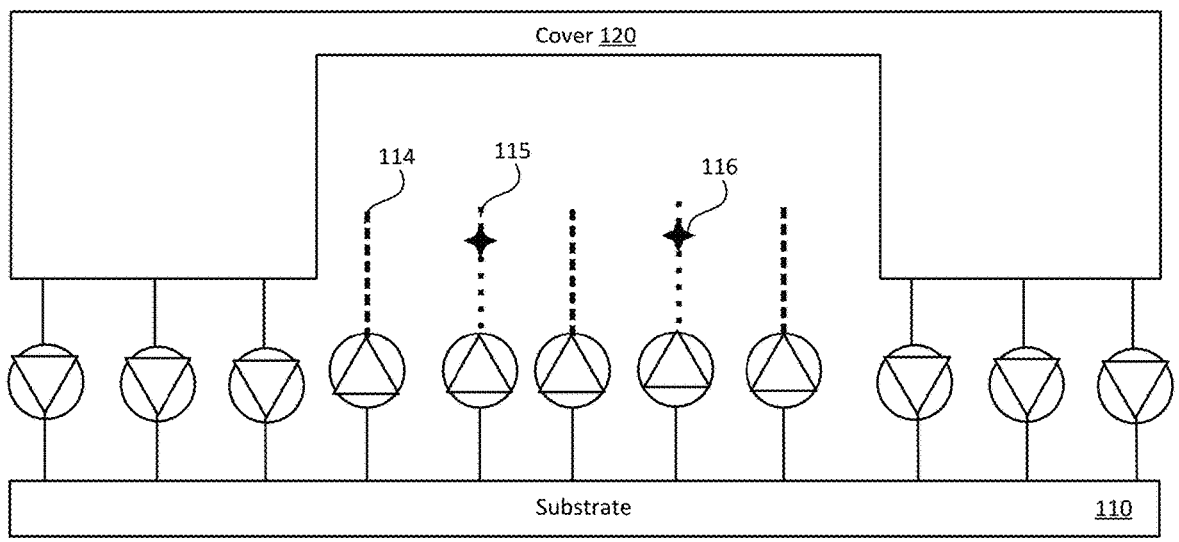

As illustrated in FIG. 7B, unprotected first moieties 113 in first region(s) 111 may be removed, while first moieties 113 in region 112 remain protected by mask 711. As illustrated in FIG. 7C, another set of first moieties 713 may be coupled to first region(s) 111 from which first moieties 113 had been removed. As illustrated in FIGS. 7D and 7E, second moieties 713 coupled to cover 120 may be reacted with first moieties 123 so as to covalently couple the cover to substrate 110. Mask 711 may be removed as illustrated in FIG. 7F so as to expose first moieties 113 in region 112. In a manner similar to that described with reference to FIG. 3C, substrate 110 then may be contacted with a fluid including oligonucleotides 114, 115 which are respectively coupled to moieties (such as moieties 713) that react with moieties to couple the oligonucleotides to second region 112. In one nonlimiting example, substrate 110 may include a layer of PAZAM, first moieties 113 may include azides of the PAZAM, first moieties 713 may include strained cycloalkynes that are coupled to substrate 110 using silanization, and second moieties 123 may include azides.

It will also be appreciated that FIGS. 1A-1D illustrate only one example of a manner in which first region(s) 121 of cover 120 may be covalently coupled to first region(s) 111 of substrate 110 using first moieties 113 and second moieties 123. Other examples may, illustratively, include disposing an intervening layer between the first region of the substrate and the first region of the cover. Covalently coupling the first region of the substrate to the first region of the cover may include covalently coupling the first region of the substrate to the intervening layer; and covalently coupling the first region of the cover to the intervening layer. For example, FIGS. 4A-4B schematically illustrate structures and operations in another example process for making a fluidic channel. Referring now to FIG. 4A, substrate 110 may include first region(s) 111 and second region 112, and cover 120 may include first region(s) 121 and second region 122. First region(s) 111 of substrate 110 may be coupled to first moieties 113, and first region(s) 121 of cover 120 also may be coupled to first moieties 113. As illustrated in FIG. 4A, intervening layer 430 (e.g., a polymer) may be disposed between first region(s) 111 of substrate 110 and first region (s) of cover 120. Intervening layer 430 may include second moieties 123. Alternatively, first region(s) 111 of substrate 110 may be coupled to second moieties 123, first region(s) 121 of cover 120 also may be coupled to second moieties 123, and intervening layer 430 may include first moieties 113. In either such example, first region(s) 121 of cover 120 may be covalently coupled to first region(s) 111 of substrate 110 using first moieties 113 and second moieties 123, and the covalent coupling between first region(s) 111 of substrate 110 and first region(s) 121 of cover 120 may suspend second region 122 of cover 120 over second region 112 of substrate 110 to form a fluidic channel. For example, in a manner such as illustrated in FIG. 4B, first moieties 113 of substrate 110 and cover 120 may react with second moieties 123 of intervening layer 430 to provide device 100 including fluidic channel 101' similar to that described with reference to FIG. 1C. It will be appreciated that any suitable number of such fluidic channels 101' may be formed to provide an assembly such as described with reference to FIG. 1D.

Figure 5A:
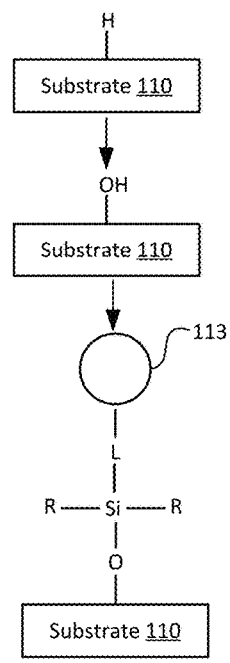
FIGS. 5A-5B schematically illustrate structures and operations in an example process for coupling moieties to substrates or covers for use in making a fluidic channel.
Figure 5B:
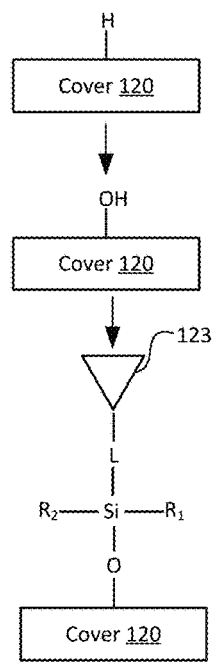
Figure 6:
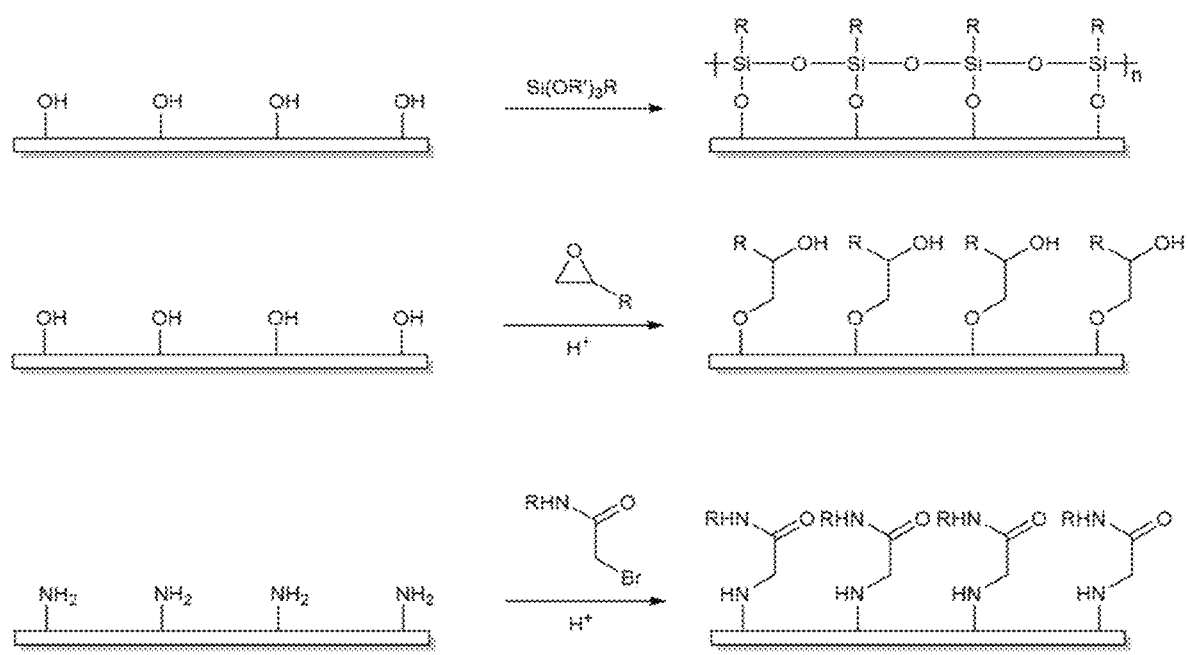
FIG. 6 schematically illustrates example reactions for coupling moieties to substrates or covers for use in making a fluidic channel.

Moieties 113 and 123 may be coupled to substrates, covers, and/or polymers (such as intervening layers) in any suitable manner. Illustratively, first moieties 113 or second moieties 123 respectively may be covalently coupled to substrate 110, cover 120, intervening layer 430, and/or polymer 312 via silane groups, carboxylate groups, or amidate groups. For example, FIGS. 5A-5B schematically illustrate structures and operations in an example process for coupling moieties to substrates or covers for use in making a fluidic channel. Referring now to FIG. 5A, in some examples the surface of substrate 110 may include —H. The —H may be converted to hydroxyl (—OH), such as illustrated in FIG. 5A, using any suitable process. It will be appreciated that some substrates may not necessarily include —H, and may be suitably processed to obtain hydroxyl groups at their surface. The hydroxyl group then may be coupled to a silane group (silanized), carboxylate group, or amidate group to which is coupled first moiety 113 or second moiety 123. In the nonlimiting example illustrated in FIG. 5A, the hydroxyl group coupled to substrate 110 is coupled to a silane group including alkyl (R) groups and a linker (L) to first moiety 113. Referring now to FIG. 5B, in some examples the surface of cover 120 may include —H. The —H may be converted to hydroxyl (—OH), such as illustrated in FIG. 5B, using any suitable process. It will be appreciated that some covers may not necessarily include —H, and may be suitably processed to obtain hydroxyl groups at their surface. The hydroxyl group then may be coupled to a silane group (silanized), carboxylate group, or amidate group to which is coupled first moiety 113 or second moiety 123, e.g., in a manner such as illustrated in FIG. 6. In the nonlimiting example illustrated in FIG. 5B, the hydroxyl group coupled to cover 120 is coupled to a silane group including alkyl (R) groups and a linker (L) to second moiety 123.

In one nonlimiting example, any alkyl C—H bonds at the surface of substrate 110 or cover 120 may be converted to C—OH bonds using confined photocatalytic oxidation (CPO) and then silanized in a manner similar to that described in Gan et al., "Photoactivation of alkyl C—H and silanization: A simple and general route to prepare high-density primary amines on inert polymer surfaces for protein immobilization," Biomacromolecules 10(5): 1238-1243 (2009), the entire contents of which are incorporated by reference herein. In examples in which moiety 113 or 123 is coupled to a polymer, e.g., polymer 312 or intervening layer 430, such polymer may be formed using monomers that include moiety 113 or moiety 123, or a precursor to such moiety, which precursor then is converted to the moiety.

It will be appreciated that cover 120 may include a different material than substrate 110, and nonetheless may be securely coupled to the substrate in a manner that is robust and may reduce or avoid disadvantages such as associated with conventional adhesives, such as chemical reactions with fluid(s) within the fluidic channel, fluorescence that may interfere with detection of a desired fluorescent signal, and/or thermal instability. In some examples, substrate 110 may include at least one material selected from the group consisting of: cyclic olefin polymer (COP), cyclic olefin copolymer (COC), glass, silicon, polypropylene (PP), photoresist, polyethylene terephthalate (PET), poly(N-(5-azido-acetamidylpentyl) acrylamide-co-acrylamide) (PAZAM), and polyethylene (PE). Independently of the material(s) used in substrate 110, cover 120 may include at least one material selected from the group consisting of: cyclic olefin polymer (COP), cyclic olefin copolymer (COC), glass, silicon, polypropylene (PP), photoresist, polyethylene terephthalate (PET), poly(N-(5-azidoacetamidylpentyl) acrylamide-co-acrylamide) (PAZAM), and polyethylene (PE). Such material(s) of the substrate and cover may be suitably coupled to first or second moieties 113, 123, and such moieties used to covalently couple the substrate to the cover in a manner such as provided herein.

In one specific, nonlimiting example, substrate 110 may include silicon disposed over tantalum oxide (Si/TaO$_x$), and cover 120 may include COC or COP. Substrate 110 may be coupled to an azide using a process that includes hydroxylating the Si surface, e.g., using a heated solution including NH$_4$OH and hydrogen peroxide, followed by silanizing the hydroxylated Si surface with an azidopropyl trimethoxysilane using spin coating or a silane oven. Cover 120 may be coupled to a DBCO using a process that includes mild peroxidation, e.g., sonication in a solution including Cu(OAc)$_2$ and hydrogen peroxide; followed by mild reductive washing, e.g., sonication in a solution including NaBH$_4$ and methanol; followed by silanizing the hydroxylated COC or COP surface with a DBCO PEG silane using spin coating or a silane oven.

Methods of Using Fluidic Devices Including Fluidic Channels

As noted elsewhere herein, oligonucleotides may be coupled to a region of a substrate within a flow channel, e.g., in a manner such as described with reference to FIGS. 1A-1D, 2A-2E, 3A-3E, 4A-4B, or 7A-7G. Oligonucleotides coupled to substrates in a manner such as described herein may be used in a variety of amplification techniques. Example techniques that can be used include, but are not limited to, polymerase chain reaction (PCR), rolling circle amplification (RCA), multiple displacement amplification (MDA), or random prime amplification (RPA), or a combination thereof. In some examples, one or more primers used for amplification may be coupled to the substrate. Formats that utilize two or more species of attached primer enable bridge amplification (BridgeAmp) or kinetic exclusion amplification (ExAmp), in which amplicons may form bridge-like structures between two attached primers that flank the template sequence that has been copied. Amplification can also be carried out with one amplification primer attached to a substrate and a second primer in solution (e.g., emulsion PCR).

Additionally, or alternatively, oligonucleotides coupled to substrates in a manner such as described herein may be used for determining the sequence of a target polynucleotide. For example, a target polynucleotide may be coupled (e.g., hybridized) to one of a plurality of primers covalently bound to a substrate in a manner such as described herein. The target polynucleotide may be amplified using the plurality of primers to form a cluster of substrate-bound amplicons. The cluster of substrate-bound amplicons may be contacted with labeled nucleotides (e.g., fluorescently labeled nucleotides) and a polymerase such that a detectable signal (e.g., fluorescence) is generated while a nucleotide is incorporated by the polymerase, and such signal may be used to identify the nucleotide and thereby determine a nucleotide sequence of the target polynucleotide.

Additional Comments

It is to be understood that any respective features/examples of each of the aspects of the disclosure as described herein may be implemented together in any appropriate combination, and that any features/examples from any one or more of these aspects may be implemented together with any of the features of the other aspect(s) as described herein in any appropriate combination to achieve the benefits as described herein.

While various illustrative examples are described above, it will be apparent to one skilled in the art that various changes and modifications may be made therein without departing from the invention. The appended claims are intended to cover all such changes and modifications that fall within the true spirit and scope of the invention.

What is claimed is:

1. A method of preparing a fluidic channel, the method comprising:
covalently coupling a first region of a substrate to a first region of a cover using first moieties covalently coupled to the first region of the substrate and second moieties covalently coupled to the first region of the cover, wherein the covalent coupling between the first region of the substrate and the first region of the cover suspends a second region of the cover over a second region of the substrate to form a fluidic channel; further comprising disposing an intervening layer between the first region of the substrate and the first region of the cover, wherein the covalently coupling the first region of the substrate to the first region of the cover comprises: covalently coupling the first region of the substrate to the intervening layer; and covalently coupling the first region of the cover to the intervening layer, wherein the covalently coupling the first region of the substrate to the intervening layer comprises a first azide-alkyne [3+2] cyclo-addition.

2. The method of claim 1, further comprising coupling oligonucleotides to the second region of the substrate.

3. The method of claim 2, wherein the oligonucleotides are coupled to the second region of the substrate before the first region of the substrate is coupled to the first region of the cover.

4. The method of claim 2, further comprising protecting the oligonucleotides before the first region of the substrate is covalently coupled to the first region of the cover.

5. The method of claim 4, wherein protecting the oligonucleotides comprises depositing a mask over the oligonucleotides.

6. The method of claim 5, further comprising removing the mask after the first region of the substrate is covalently coupled to the first region of the cover.

7. The method of claim 2, wherein the oligonucleotides are covalently coupled to the second region of the substrate using second moieties covalently coupled to the second region of the substrate.

8. The method of claim 2, wherein the oligonucleotides comprise capture primers.

9. The method of claim 2, wherein the oligonucleotides are coupled to the second region of the substrate after the first region of the substrate is coupled to the first region of the cover.

10. The method of claim 1, wherein covalently coupling the first region of the substrate to the first region of the cover comprises selectively applying heat to the first region of the substrate or the first region of the cover.

11. The method of claim 10, wherein the heat is applied using light.

12. The method of claim 11, wherein the light includes an infrared or near-infrared wavelength.

13. The method of claim 1, wherein covalently coupling the first region of the substrate to the first region of the cover comprises applying pressure to the first region of the substrate and the first region of the cover.

14. The method of claim 1, wherein the intervening layer comprises the first moieties or the second moieties.

15. The method of claim 1, wherein covalently coupling the first region of the cover to the intervening layer comprises a comprises a second azide-alkyne [3+2] cyclo-addition.

16. The method of claim 1, wherein the first moieties are covalently coupled to the first region of the substrate via silane groups, carboxylate groups, or amidate groups.

17. The method of claim 1, wherein the second moieties are covalently coupled to the second region of the substrate via silane groups, carboxylate groups, or amidate groups.

18. The method of claim 1, wherein the cover comprises a different material than the substrate.

19. The method of claim 1, wherein the cover comprises at least one material selected from the group consisting of: cyclic olefin polymer (COP), cyclic olefin copolymer (COC), glass, silicon, polypropylene (PP), photoresist, polyethylene terephthalate (PET), poly(N-(5-azidoacetamidylpentyl) acrylamide-co-acrylamide) (PAZAM), and polyethylene (PE).

20. The method of claim 1, wherein the substrate comprises at least one material selected from the group consisting of: cyclic olefin polymer (COP), cyclic olefin copolymer (COC), glass, silicon, polypropylene (PP), photoresist, polyethylene terephthalate (PET), poly(N-(5-azidoacetamidylpentyl) acrylamide-co-acrylamide) (PAZAM), and polyethylene (PE).

21. The method of claim 1, wherein the second region of the cover is separated from the second region of the substrate by between about 1 μm and about 1 cm.

* * * * *

UNITED STATES PATENT AND TRADEMARK OFFICE
CERTIFICATE OF CORRECTION

PATENT NO. : 12,398,422 B2
APPLICATION NO. : 17/743969
DATED : August 26, 2025
INVENTOR(S) : Steven Modiano et al.

Page 1 of 1

It is certified that error appears in the above-identified patent and that said Letters Patent is hereby corrected as shown below:

In the Claims

Column 26, Line 15:
In Claim 15, delete "a comprises a second" and insert -- a second --.

Signed and Sealed this
Ninth Day of December, 2025

John A. Squires
*Director of the United States Patent and Trademark Office*